United States Patent
Kasahara et al.

(10) Patent No.: US 7,316,683 B2
(45) Date of Patent: Jan. 8, 2008

(54) TREATMENT DEVICE FOR CUTTING LIVING TISSUE

(75) Inventors: Hideyuki Kasahara, Musashino (JP); Takahiro Kogasaka, Hino (JP)

(73) Assignee: Olympus Corporation (JP)

( * ) Notice: Subject to any disclaimer, the term of this patent is extended or adjusted under 35 U.S.C. 154(b) by 0 days.

(21) Appl. No.: 10/329,945

(22) Filed: Dec. 24, 2002

(65) Prior Publication Data
US 2003/0130654 A1 Jul. 10, 2003

(30) Foreign Application Priority Data
Dec. 28, 2001 (JP) ............... 2001-401941
Dec. 28, 2001 (JP) ............... 2001-401942

(51) Int. Cl.
*A61B 18/18* (2006.01)

(52) U.S. Cl. ...................................... 606/45

(58) Field of Classification Search ............ 606/27–52
See application file for complete search history.

(56) References Cited

U.S. PATENT DOCUMENTS

| | | | |
|---|---|---|---|
| 3,987,795 A | 10/1976 | Morrison | 128/303.14 |
| 5,445,638 A | 8/1995 | Rydell et al. | 606/51 |
| 5,586,991 A * | 12/1996 | Yoon | 606/185 |
| 5,817,013 A * | 10/1998 | Ginn et al. | 600/114 |
| 5,899,912 A | 5/1999 | Eaves, III | 606/159 |
| 6,019,771 A | 2/2000 | Bennett et al. | 606/159 |
| 6,022,313 A * | 2/2000 | Ginn et al. | 600/114 |
| 6,030,383 A | 2/2000 | Benderev | |
| 6,165,175 A * | 12/2000 | Wampler et al. | 606/48 |
| 6,210,409 B1 | 4/2001 | Ellman et al. | |
| 6,428,539 B1 * | 8/2002 | Baxter et al. | 606/49 |
| 6,443,970 B1 * | 9/2002 | Schulze et al. | 606/171 |
| 6,572,615 B2 * | 6/2003 | Schulze et al. | 606/50 |
| 6,592,582 B2 * | 7/2003 | Hess et al. | 606/49 |
| 6,602,251 B2 * | 8/2003 | Burbank et al. | 606/45 |
| 6,669,709 B1 * | 12/2003 | Cohn et al. | 606/167 |
| 6,770,071 B2 * | 8/2004 | Woloszko et al. | 606/41 |
| 6,818,003 B2 * | 11/2004 | Genovesi | 606/159 |
| 6,923,759 B2 * | 8/2005 | Kasahara et al. | 600/157 |

FOREIGN PATENT DOCUMENTS

GB 2 308 980 A 7/1997
WO WO 98/16162 4/1998

OTHER PUBLICATIONS

Search Report from European Patent Office dated Apr. 28, 2003.
English translation of Japanese Office Action dated Oct. 25, 2005.

* cited by examiner

*Primary Examiner*—Roy D. Gibson
*Assistant Examiner*—Pete Vrettakos
(74) *Attorney, Agent, or Firm*—Ostrolenk, Faber, Gerb & Soffen, LLP

(57) ABSTRACT

According to one aspect of the present invention, there is provided a treatment device for cutting a living tissue, comprising a main unit which is to be inserted into a body, a tip-end treatment portion which is disposed at a tip end of the main unit to cut the living tissue, a notch groove which is disposed at the tip-end treatment portion and which compresses the living tissue guided into the notch groove, and an electrode which is positioned in a part of the notch groove and which electrically cuts the living tissue compressed by the notch groove.

20 Claims, 25 Drawing Sheets

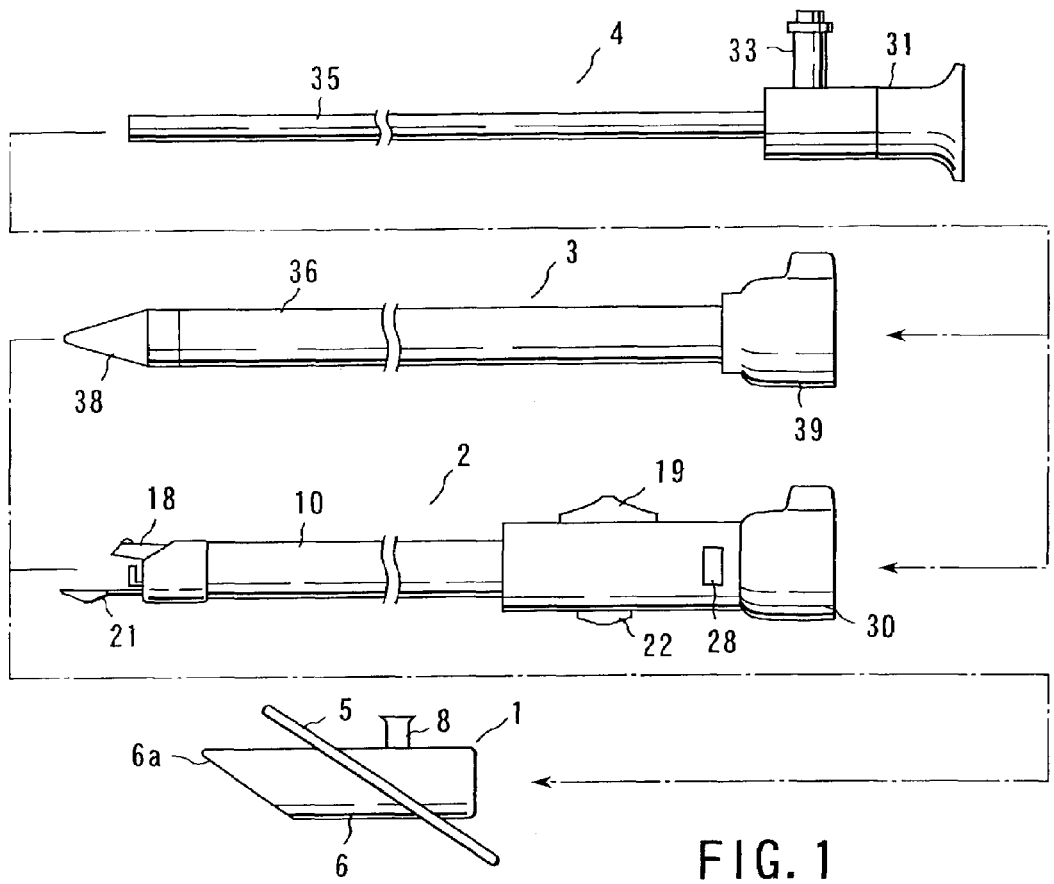
FIG. 1
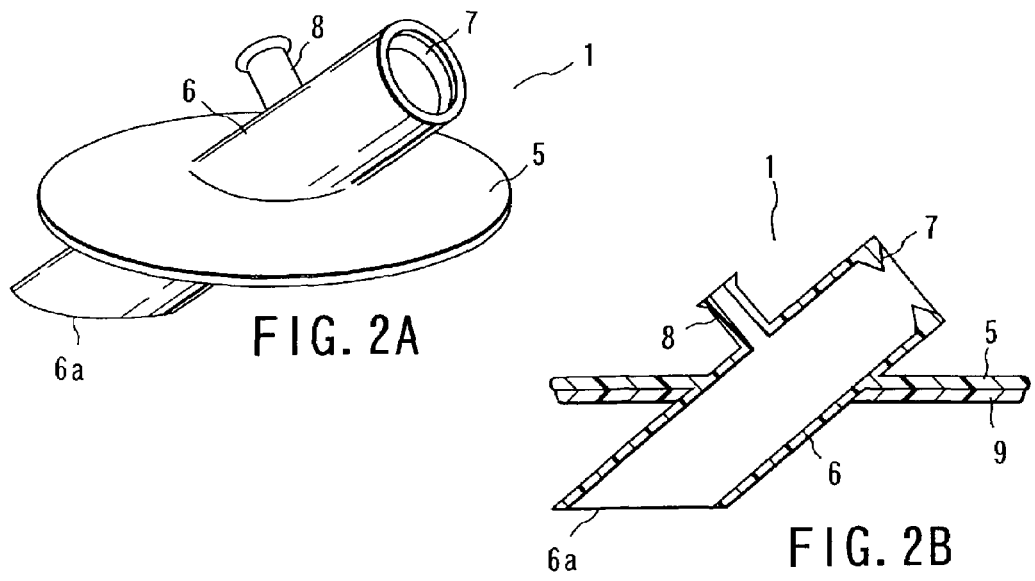
FIG. 2A
FIG. 2B

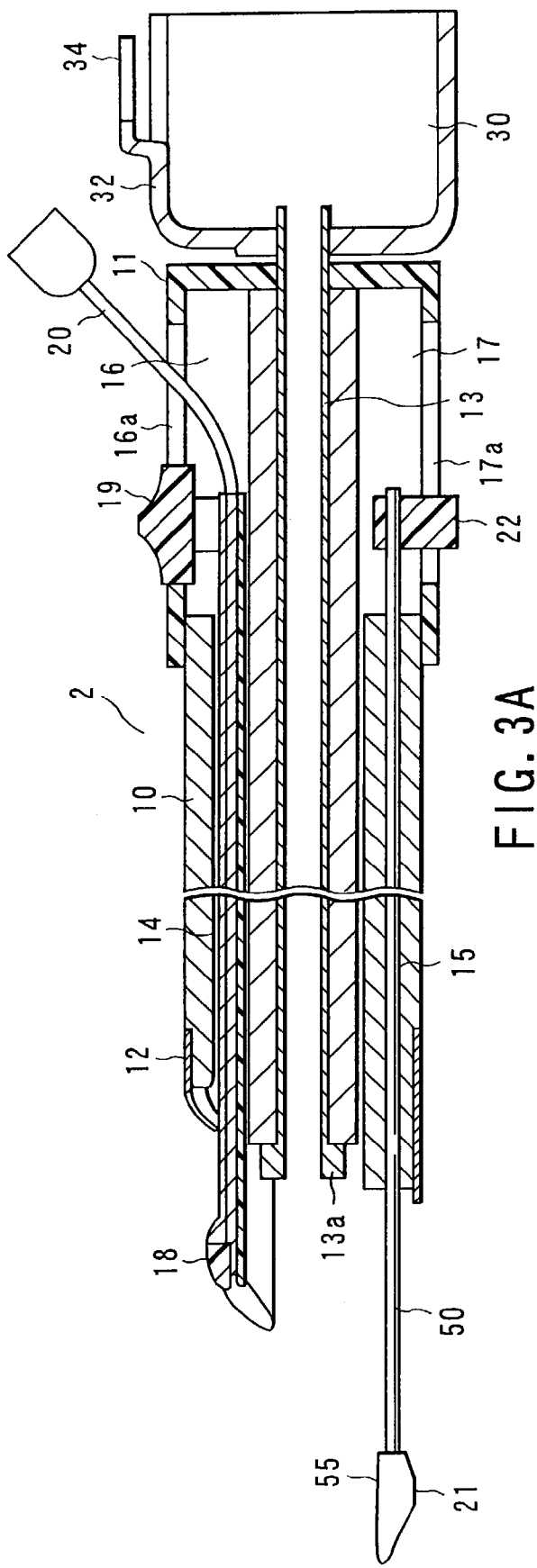
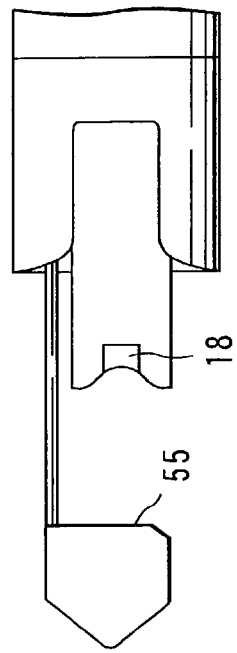
FIG. 3A
FIG. 3B

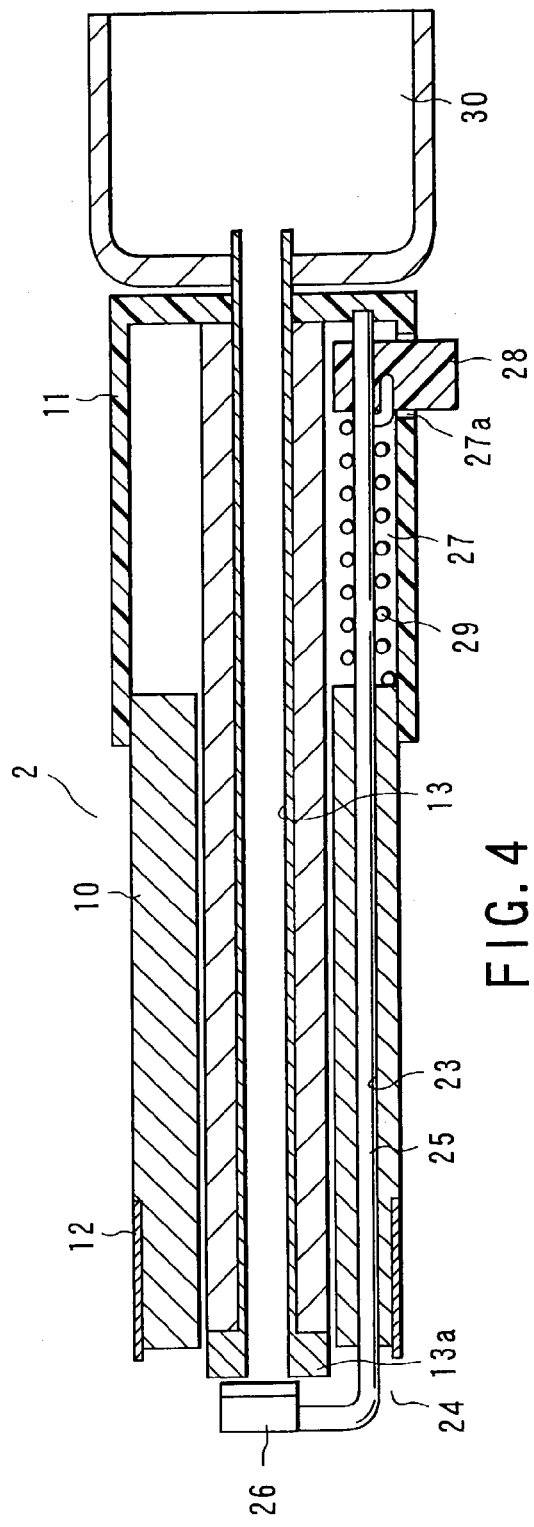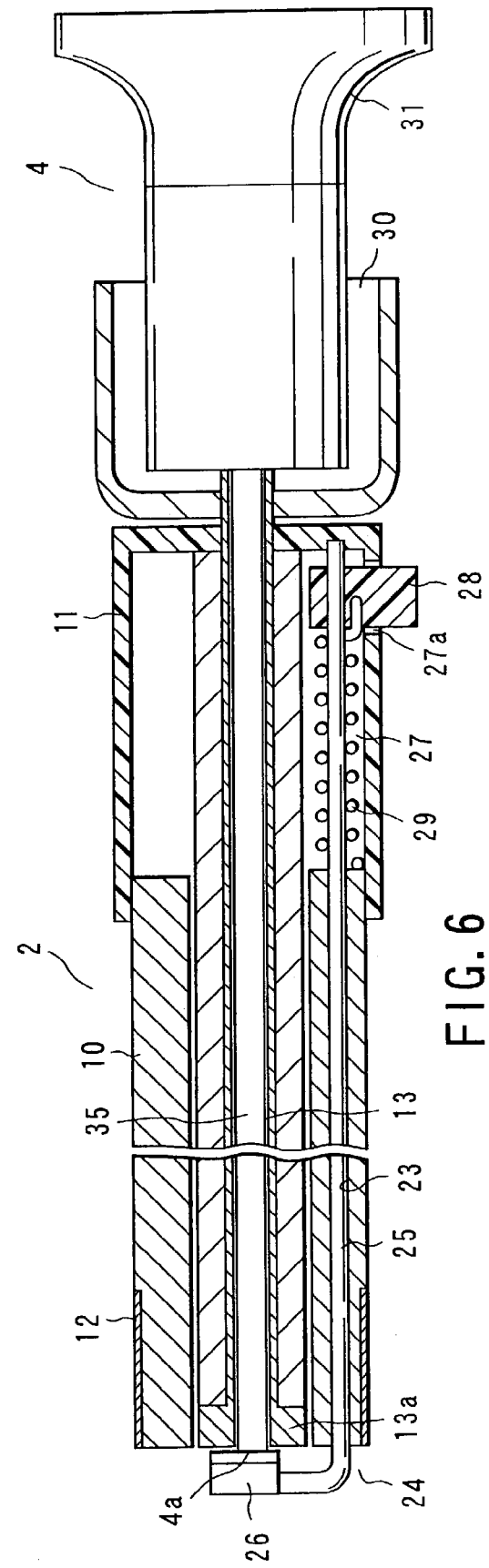

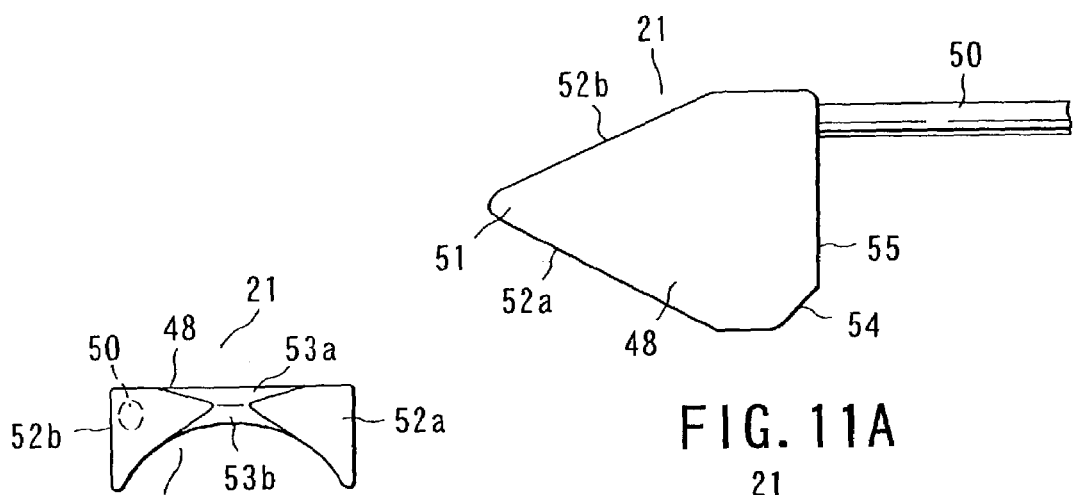
FIG. 11A
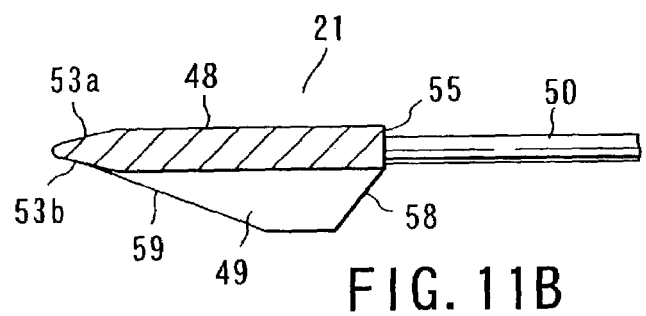
FIG. 11B
FIG. 11C
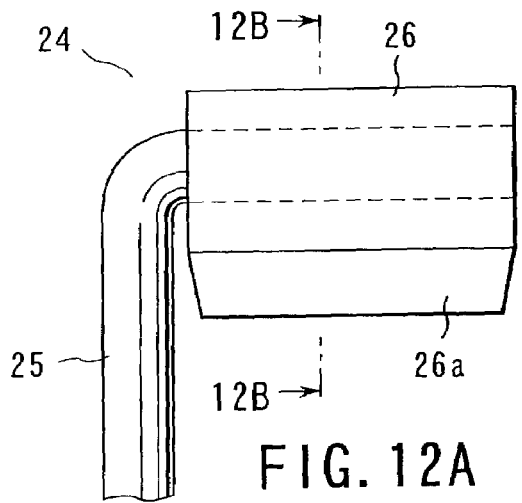
FIG. 12A
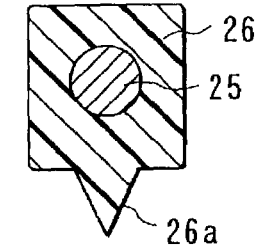
FIG. 12B
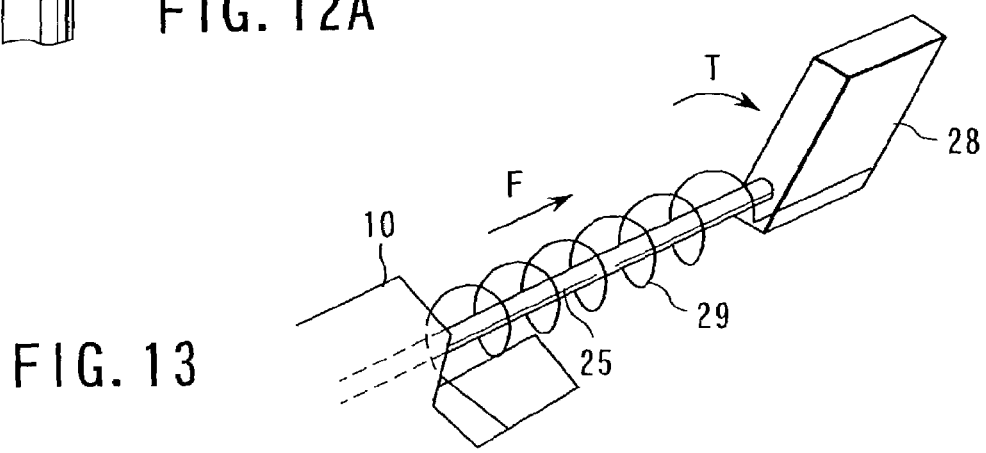
FIG. 13

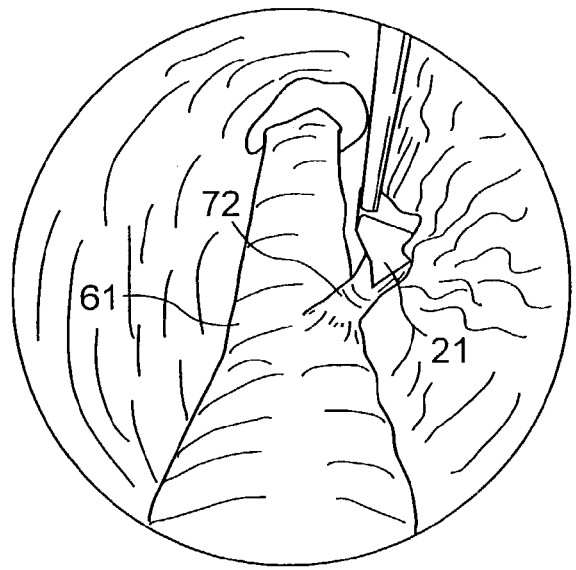
FIG. 20
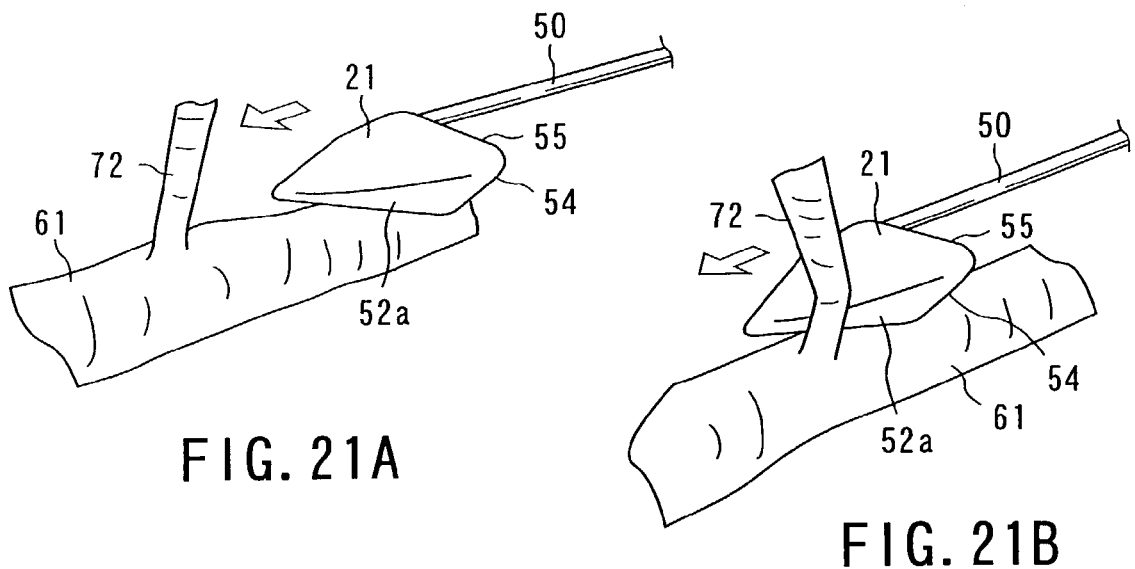
FIG. 21A
FIG. 21B
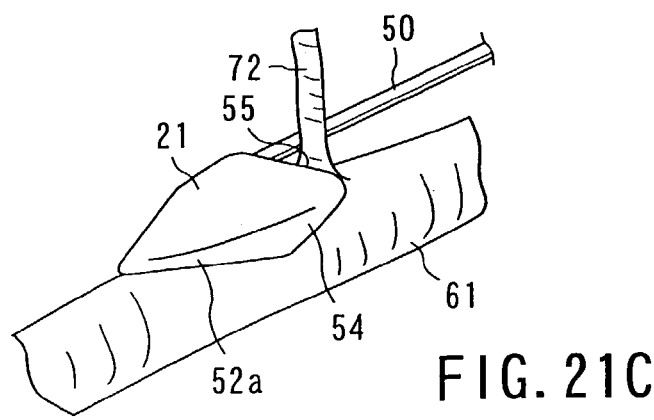
FIG. 21C

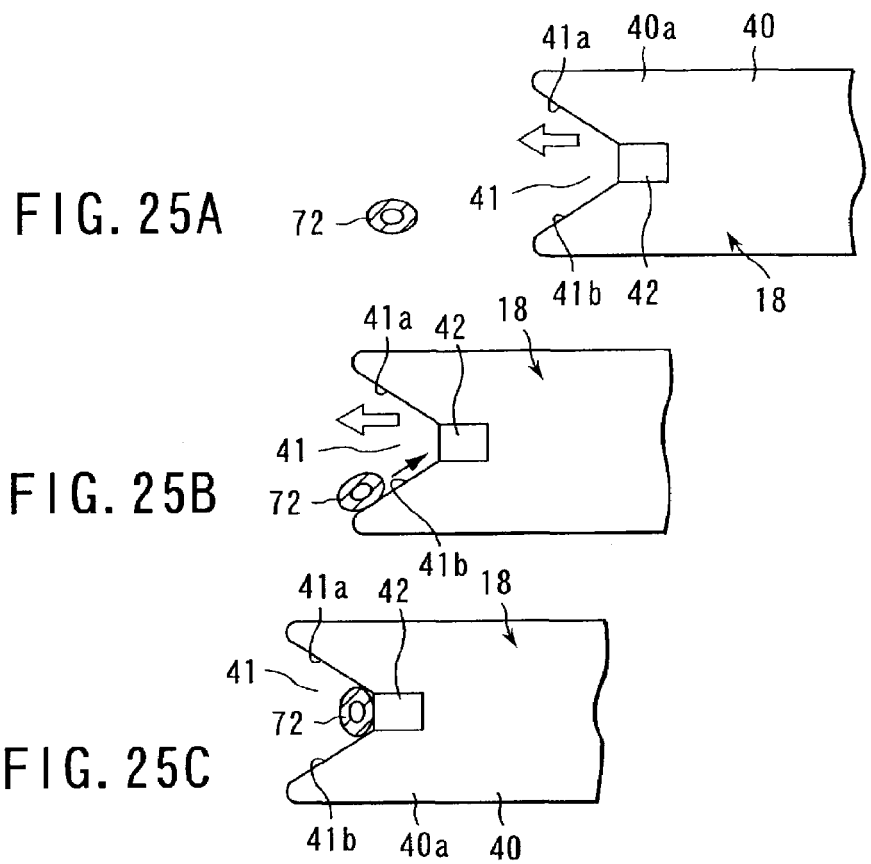
FIG. 25A
FIG. 25B
FIG. 25C
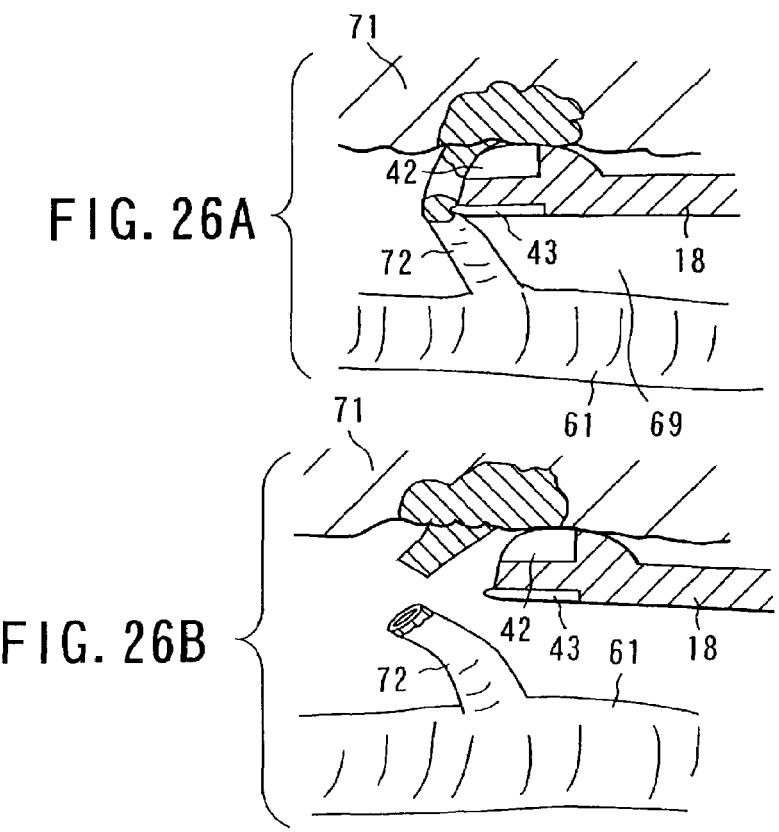
FIG. 26A
FIG. 26B

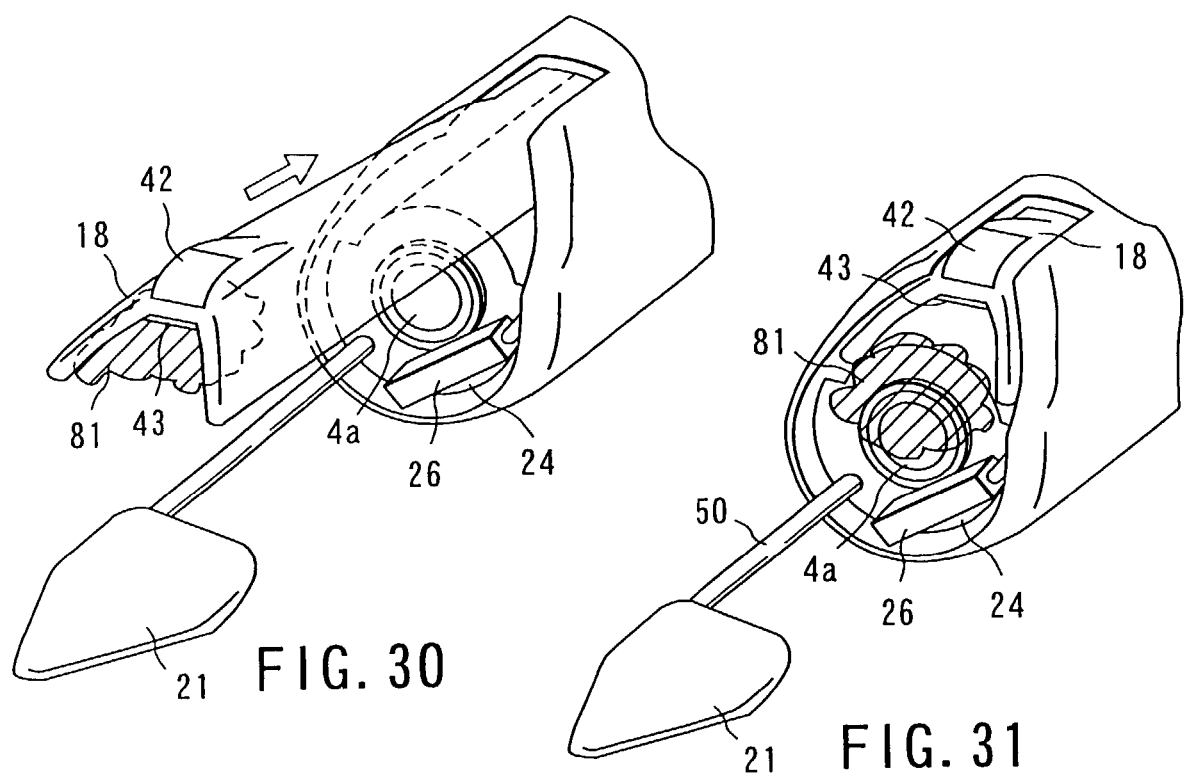

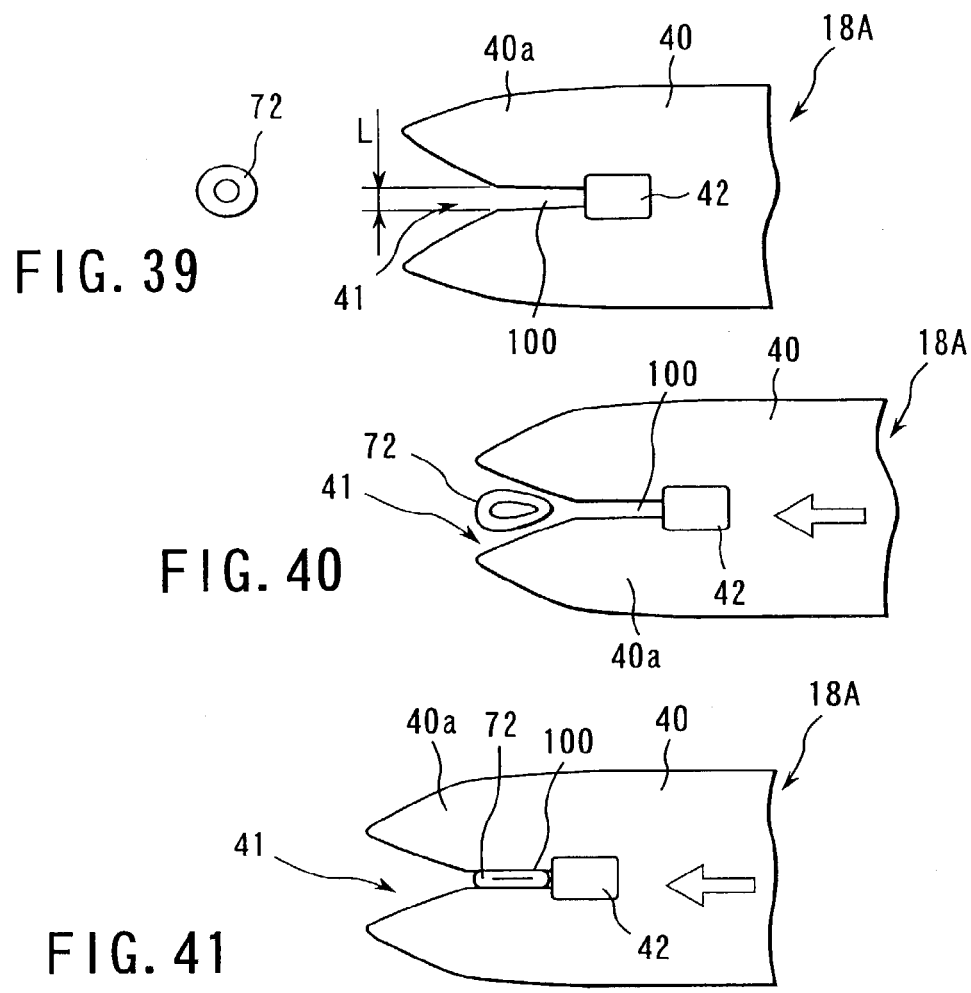
FIG. 39
FIG. 40
FIG. 41
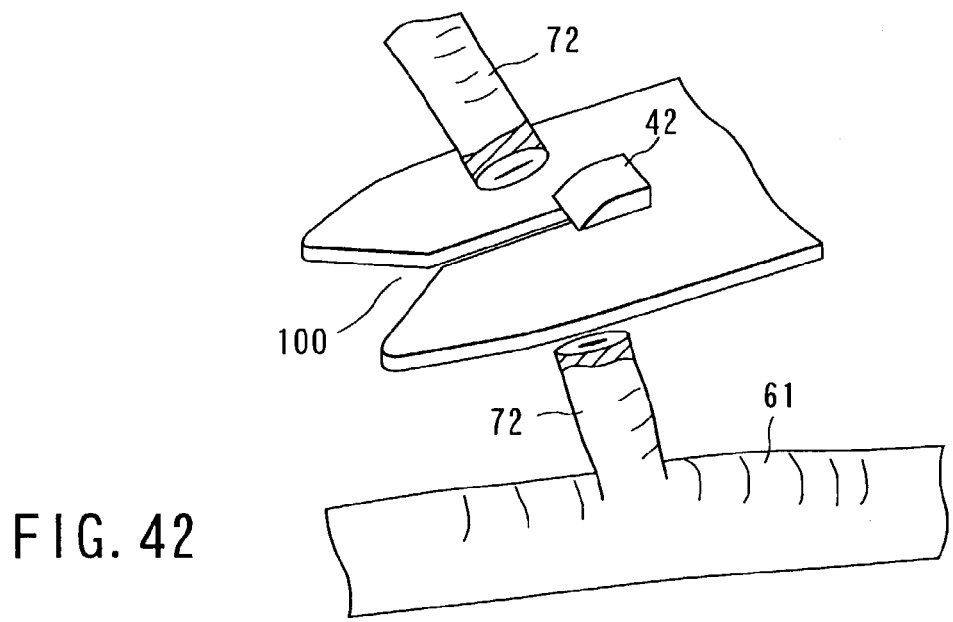
FIG. 42

TREATMENT DEVICE FOR CUTTING LIVING TISSUE

CROSS-REFERENCE TO RELATED APPLICATIONS

This application is based upon and claims the benefit of priority from the prior Japanese Patent Applications No. 2001-401941, filed Dec. 28, 2001, and No. 2001-401942, filed Dec. 28, 2001, the entire contents of both of which are incorporated herein by reference.

BACKGROUND OF THE INVENTION

1. Field of the Invention

The present invention relates to a living tissue cutting treatment device for cutting living tissues such as a blood vessel.

2. Description of the Related Art

Various electric treatment devices of monopolar type and bipolar type are known, which are configured to cut living tissues such as a blood vessel. U.S. Pat. No. 5,445,638, for example, discloses a treatment device comprising a pair of jaws that have an electrode each. The jaws can be opened and closed. When closed, the jaws clamp a blood vessel. While the blood vessel is so clamped, a current is made to flow in the electrodes, coagulating the clamped part of the blood vessel. The blood vessel is thereby cut. Another type of a treatment device is known, which has a blade that is moved to cut a blood vessel.

With these conventional treatment devices, surgeons cannot cut a blood vessel when the treatment portion (electrode portion) is simply pressed onto the object blood vessel. They cannot cut blood vessels unless the jaws are opened and closed or the blade pressed on the blood vessel is moved back and forth.

BRIEF SUMMARY OF THE INVENTION

An object of the present invention is to provide a treatment device for coagulating and cutting a living tissue, which can easily cut living tissues such as a blood vessel.

The object of the present invention is achieved by the following treatment device for cutting a living tissue. That is, according to one aspect of the present invention, there is provided a treatment device for cutting a living tissue, comprising: a main unit which is to be inserted in a body; a tip-end treatment portion which is disposed at a tip end of the main unit to cut the living tissue; a notch groove which is disposed at the tip-end treatment portion and into which the living tissue is introduced to thereby compress this living tissue; and an electrode which is positioned in a part of the notch groove and which coagulates and electrically cuts the living tissue compressed by the notch groove.

BRIEF DESCRIPTION OF THE SEVERAL VIEWS OF THE DRAWING

FIG. 1 is an exploded side view of a living tissue harvesting apparatus according to a first embodiment of the present invention;

FIG. 2A is a perspective view of a trocar;

FIG. 2B is a longitudinal sectional side view of the trocar;

FIG. 3A is a longitudinal sectional side view of a treatment sheath from which a rigid endoscope is removed;

FIG. 3B is a plan view of a tip end of the treatment sheath of FIG. 3A;

FIG. 4 is a longitudinal sectional plan view of the treatment sheath from which the rigid endoscope is removed;

FIG. 6 is a longitudinal sectional plan view of the treatment sheath through which the rigid endoscope is inserted;

FIG. 11A is a top plan view of a blood vessel holder;

FIG. 11B is a longitudinal sectional side view of the blood vessel holder;

FIG. 11C is a front view of the blood vessel holder;

FIG. 12A is a top plan view of a wiper;

FIG. 12B is a sectional view taken along a line 12B-12B of FIG. 12A;

FIG. 13 is a perspective view of a wiper operation portion;

FIG. 20 is a diagram showing the monitor image;

FIGS. 21A to 21C are perspective views showing a function of the blood vessel holder;

FIGS. 25A to 25C are plan views showing the function of the bipolar cutter;

FIGS. 26A and 26B are sectional views inside the body showing the function of the bipolar cutter;

FIG. 30 is a perspective view of the tip end of the treatment sheath;

FIG. 31 is a perspective view of the tip end of the treatment sheath;

FIG. 39 is a plan view showing a first stage of the use mode of the bipolar cutter of FIG. 32A;

FIG. 40 is a plan view showing a second stage of another use mode of the bipolar cutter of FIG. 32A;

FIG. 41 is a plan view showing a third stage of the other use mode of the bipolar cutter of FIG. 32A;

FIG. 42 is a perspective view showing a fourth stage of the other use mode of the bipolar cutter of FIG. 32A;

DETAILED DESCRIPTION OF THE INVENTION

Figure 5:
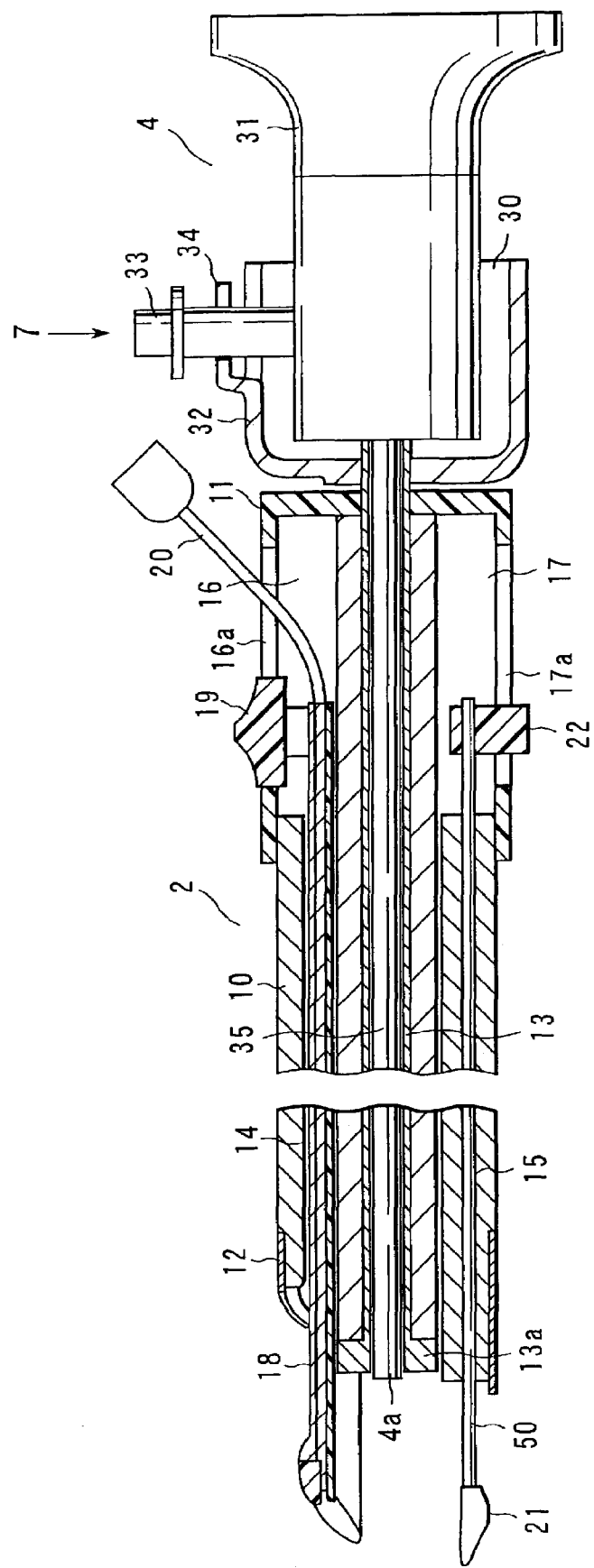
FIG. 5 is a longitudinal sectional side view of the treatment sheath through which the rigid endoscope is inserted.

Embodiments of the present invention will be described hereinafter with reference to the drawings.

FIG. 1 shows an endoscopic blood vessel harvesting apparatus as a living tissue harvesting apparatus in which a treatment device for cutting a living tissue according to a first embodiment of the present invention is incorporated. This apparatus is constituted of: a trocar 1; a treatment sheath 2; a dissector 3 as expansion means; and a rigid endoscope 4 as an endoscope.

As shown in FIGS. 2A and 2B, the trocar 1 is integrally molded of a synthetic resin material, and a cylindrical guide tube 6 is obliquely inserted through a substantially disc-shaped flange 5. The inner and outer surfaces of the guide tube 6 are coated with a lubricant in order to improve slip at an insertion time. A tip end 6a of the guide tube 6 is cut at an acute angle, and the end surface of the tip end 6a is formed substantially in parallel to the flange 5.

Furthermore, an airtight ring portion 7 is integrally disposed in an inner peripheral surface in a base end of the guide tube 6, and an air supply head 8 is integrally disposed in a middle portion. Moreover, an adhesive layer 9 such as an adhesive tape is disposed on the lower surface of the flange 5, and the trocar 1 can be fixed so as to adhere to a scurf skin.

The treatment sheath 2 will next be described. The sheath is constituted as shown in FIGS. 3A, 3B and 4. A sheath main unit 10 is a straight cylindrical member formed of a synthetic resin material, and the surface of the unit is coated with a lubricant to improve slip at an insertion time. An operation portion cover 11 constituting a grasp portion is attached to a proximal end of the sheath main unit 10, and a tip end cover 12 is attached to a distal end.

As shown in FIGS. 3A and 3B, an endoscope channel 13 is disposed over the whole length of an axial center portion of the sheath main unit 10. The proximal end of the endoscope channel 13 projects on a hand side through the operation portion cover 11, and a flange portion 13a projecting from the front end surface of the sheath main unit 10 is disposed in a distal end. A first treatment device channel 14 is disposed in a portion eccentric upwards and a second treatment device channel 15 is disposed in a portion eccentric downwards so that the endoscope channel 13 is held between the channels in the sheath main unit 10. Therefore, the first treatment device channel 14 and second treatment device channel 15 are substantially symmetrically arranged in positions most apart from each other via the endoscope channel 13.

The proximal end of the first treatment device channel 14 opens in a first slide operation portion 16 inside the operation portion cover 11, and the proximal end of the second treatment device channel 15 opens in a second slide operation portion 17 in the operation portion cover 11. A bipolar cutter 18 as a treatment device for cutting a living tissue described later is inserted through the first treatment device channel 14 so that the cutter can move forwards/backwards in an axial direction, and a treatment device operation portion 19 is disposed in a range of an elongate hole 16a of the first slide operation portion 16 of the first slide operation portion 16 in the proximal end so that the portion can slide in the axial direction. When the treatment device operation portion 19 is pulled to the proximal end, the distal end of the bipolar cutter 18 can be held in the first treatment device channel 14. Moreover, the bipolar cutter 18 is connected to a bipolar cable 20, and the bipolar cable 20 is driven toward the outside through the elongate hole 16a A blood vessel holder 21 as a blood vessel holding member described later is inserted through the second treatment device channel 15 in such a manner that the holder can move forwards/backwards in the axial direction, and a holder operation portion 22 is disposed in a range of an elongate hole 17a of the second slide operation portion 17 in the proximal end in such a manner that the portion can slide in the axial direction.

Furthermore, as shown in FIG. 4, a through hole 23 is disposed in the axial direction in one side portion of the endoscope channel 13 inside the sheath main unit 10. A wiper rod 25 of a wiper 24 described later is inserted through the through hole 23 in such a manner that the rod can rotate. The distal end of the wiper rod 25 is bent substantially in an L shape, and a wiper rubber 26 is disposed on the tip end of the rod.

The proximal end of the wiper rod 25 extends to a rotating operation portion 27 inside the operation portion cover 11, and is rotatably supported on the inner wall of the operation portion cover 11. A wiper operation portion 28 is fixed to the proximal end of the wiper rod 25, and the wiper operation portion 28 can rotate in a range of an elongate hole 27a which extends in a peripheral direction of the operation portion cover 11.

Moreover, an endoscope holding portion 30 is disposed on the hand side of the operation portion cover 11 in a fixed state with respect to the endoscope channel 13. The endoscope holding portion 30 includes a sufficient cavity for containing an eyepiece portion 31 of the rigid endoscope 4, and a cutout portion 34 into which a light guide head 33 disposed on the eyepiece portion 31 is inserted/engaged is formed in a part (upper part) of a peripheral wall 32.

Figure 7:
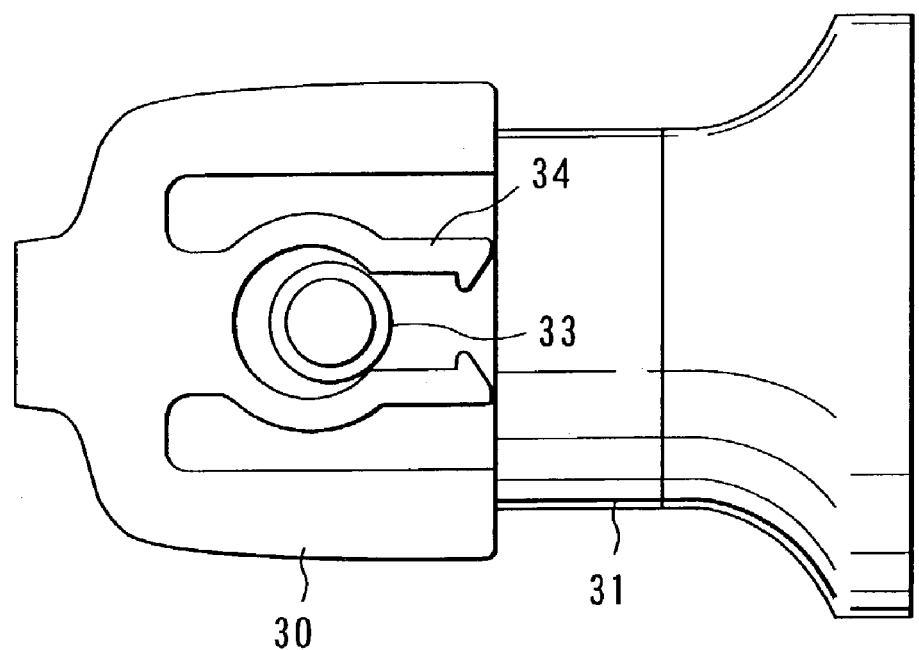
FIG. 7 is a diagram seen from an arrow 7 direction of FIG. 5.

Therefore, as shown in FIGS. 5 to 7, an insertion portion 35 of the rigid endoscope 4 is inserted into the endoscope channel 13, the light guide head 33 is inserted/engaged into the cutout portion 34 so as to hold the eyepiece portion 31 in the endoscope holding portion 30, the rigid endoscope 4 is then held with respect to the treatment sheath 2 and positioned in the axial direction. The sheath main unit 10 and the operation portion cover 11 are secured to the endoscope channel 13 and can rotate. The endoscope channel 13 and endoscope holding portion 30 are fixed. Hence, that part of the treatment sheath 2 which is more distal from the cover 11 than the rigid endoscope 4 can be held and rotate in rotatable state, as long as the treatment sheath 2 and the rigid endoscope 4 remain coupled together.

The bipolar cutter 18 will next be described.

As shown in FIGS. 9A to 10C, the bipolar cutter 18 includes: a cutter main unit 40 which is inserted in a body; a tip-end treatment portion 40a which is disposed in the tip end of the cutter main unit 40 to cut the blood vessel; and electrodes 42, 43 which are disposed in the tip-end treatment portion 40a to electrically cut the blood vessel. The cutter main unit 40 is formed of an insulating member (including a ceramic member) such as a synthetic resin material, and has a shape of a strip plate member bent in a arc shape along a arc inner peripheral surface of the sheath main unit 10. The curved shape (roof shape) of the cutter main unit 40 prevents the tissue from sagging from the upper side (presses/discharges a fat tissue in a body cavity) as described later, and is useful for securing the view field of the rigid endoscope 4.

A guide portion for guiding the blood vessel into the electrodes 42 and 43 with the movement of the cutter main unit 40 in the axial direction is formed in the tip-end treatment portion 40a of the cutter main unit 40. In the present embodiment, the guide portion is formed by a notch groove (slit) 41 cut in a V shape. In this case, sides 41a, 41b forming the V shape extend upwards to the top portion of the arc portion on the proximal-end side from opposite edges of the distal end of the cutter main unit 40, and form a tissue guide surface of the notch groove (hereinafter referred to as the V groove) 41 which tapers on the proximal-end side.

A pair of electrodes 42, 43 disposed opposite to each other are fixed/disposed on a bottom of the V groove 41, that is, an intersection of the respective sides 41a, 41b forming the V shape. The electrodes 42, 43 are not disposed in the same plane, and are positioned vertically opposite to each other.

Of these two electrodes, the upper electrode 42 has a surface area larger than that of the lower electrode 43. That is, the upper electrode 42 contacts tissues at a large area, whereas the lower electrode 43 contacts tissues at a small area. Hence, the lower electrode 42 is used mainly as a cutting electrode, and the upper electrode 43 is used mainly as a coagulation electrode.

Figure 27:
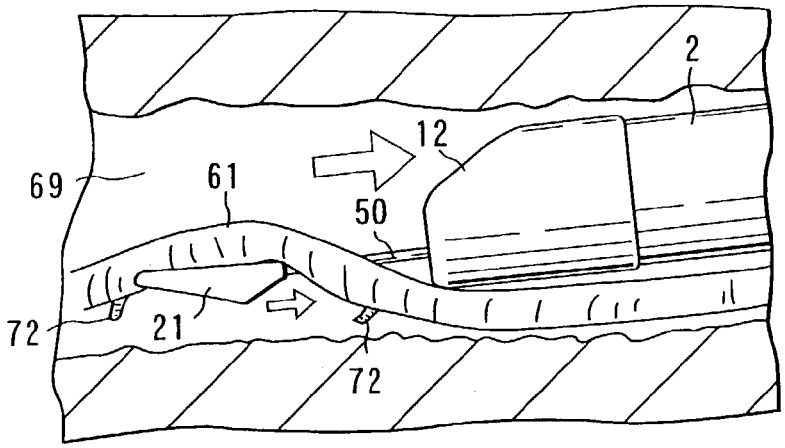
FIG. 27 is a sectional view inside the body in the treatment state.

In general, the electrode having a large contact area is higher than the electrode having a small contact area in a bleeding stop capability at an incision time. As described later (see FIGS. 26A to 27), an incised portion of the incised side branch 72 of the extracted blood vessel 61 is bound with a ligature after extracting the blood vessel 61. However, the incised portion on a patient side remains in the body as such, it is preferable to stop the bleeding. Therefore, in the present embodiment, the electrode 43 functioning as the incision electrode and having the small contact area is disposed on a lower side, that is, on a side of the blood vessel 61 to be extracted (the side of the blood vessel holder 21 for holding the blood vessel 61 as described later). The electrode 42 which functions as the coagulation electrode and has the large contact area is disposed on an upper side, that is, on the body side (the side remaining in the body). Moreover, a reason why the electrode 42 having the large contact area is disposed on the upper side, that is, the body side is that the body-side electrode 42 is disposed as far from the blood vessel 61 to be harvested as possible and thermal influence onto the blood vessel 61 is minimized. Hereinafter, the upper electrode 42 will be referred to as "body-side electrode," and the lower electrode 43 will be referred to as "cut electrode."

The body-side electrode 42 and cut electrode 43 are connected to lead wires 44, 45, and these lead wires 44, 45 are laid along the upper and lower surfaces of the cutter main unit 40, and connected to the bipolar cable 20. Furthermore, the lead wires 44, 45 are coated with insulating films 46, 47, and insulated. It is to be noted that portions of the bipolar cutter 18 other than the electrodes 42, 43 may also be formed by a transparent material (acryl, and the like).

The blood vessel holder 21 according to the present embodiment will next be described in detail with reference to FIGS. 11A to 11C. As shown in FIGS. 11A to 11C, the blood vessel holder 21 includes one operation rod 50 as a shaft portion which is moved forwards/backwards in the sheath main unit 10, and a main unit which is disposed in the tip end of the operation rod 50 to hold the harvesting object blood vessel 61. The main unit is formed of the synthetic resin material substantially in a triangular shape in a plan view, the upper surface is formed in a flat surface 48, and the lower surface is formed in a arc concave surface 49 which forms a press groove to press the harvested blood vessel 61. This arc concave surface 49 functions as a press discharge portion which presses/discharges the harvested blood vessel 61 in a direction apart from the bipolar cutter 18 as described later. Moreover, the operation rod 50 is connected to a lopsided position in a rear-end portion of the blood vessel holder 21 (the operation rod 50 is connected to a position eccentric from a center axis of the main unit of the blood vessel holder 21). It is to be noted that the operation rod 50 is inserted through the second treatment device channel 15 so as to be movable forwards/backwards.

The tip end of the blood vessel holder 21 is formed as an acute-angled stripping portion 51 for stripping the tissue. Moreover, first left and right taper surfaces 52a, 52b are symmetrically formed in the blood vessel holder 21 so as to be linked from the stripping portion 51. That is, the tip end of the main unit is formed in a taper shape which tapers at the acute angle. Furthermore, inclined surfaces 53a, 53b are formed in upper and lower surfaces of the stripping portion 51 toward the tip end so that the upper and lower surfaces have a small width. A hem portion of the first taper surface 52a on a side opposite to the connected portion of the blood vessel holder 21 to the operation rod 50 is formed on a second taper surface 54 which has a arc shape, and the second taper surface 54 is continued to a hook portion 55 including a flat surface which is positioned in the rear end of the blood vessel holder 21 so as to catch the blood vessel. That is, the main unit further includes the rear end for catching the living tissue. Concretely, as shown in FIG. 3B, the hook portion 55 is disposed in a position opposite to the bipolar cutter 18 in the axial direction.

Opposite side walls of the blood vessel holder 21 forming the arc concave surface 49 include a third taper surface 59 which extends downwards from the stripping portion 51, and a fourth taper surface 58 which extends downwards from the hook portion 55.

The wiper 24 will be described in detail. The wiper is constituted as shown in FIGS. 12A and 12B. That is, the wiper rubber 26 fixed to the distal end of the wiper rod 25 is fixed to an L-shaped folded portion of the wiper rod 25 by adhesion or insert molding, and is disposed at right angles to the axial direction. The wiper rubber 26 includes a scraping portion 26a which has a triangular section and flexibility. Thereby, by rotation of the wiper rubber 26, foreign particles sticking to the objective lens surface 4a of the rigid endoscope 4, such as blood, mucosa, and fat, can be scraped off. In this case, the scraping portion 26a has flexibility. Therefore, even when a stepped portion is generated between the tip end surface of the sheath main unit 10 and the objective lens surface 4a, the rubber goes beyond the stepped portion and slides against the objective lens surface 4a.

As shown in FIG. 13, one end of the torsion coil spring 29 including the coil spring disposed on the wiper rod 25 of the wiper 24 abuts on the end surface of the sheath main unit 10, and the other end is disposed between the unit and the wiper operation portion 28 in a compressed state and is further engaged with the side surface of the wiper operation portion 28. Therefore, the torsion coil spring 29 generates a rotation torque T for rotating the wiper rod 25 in one direction, and a force F for urging the wiper rod 25 toward the proximal end direction of the sheath main unit 10. Thereby, the wiper rubber 26 is urged in a direction in which the rubber retreats to the side of the objective lens surface 4a of the rigid endoscope 4, and a direction in which the rubber contacts the objective lens surface 4a.

Figure 9A:
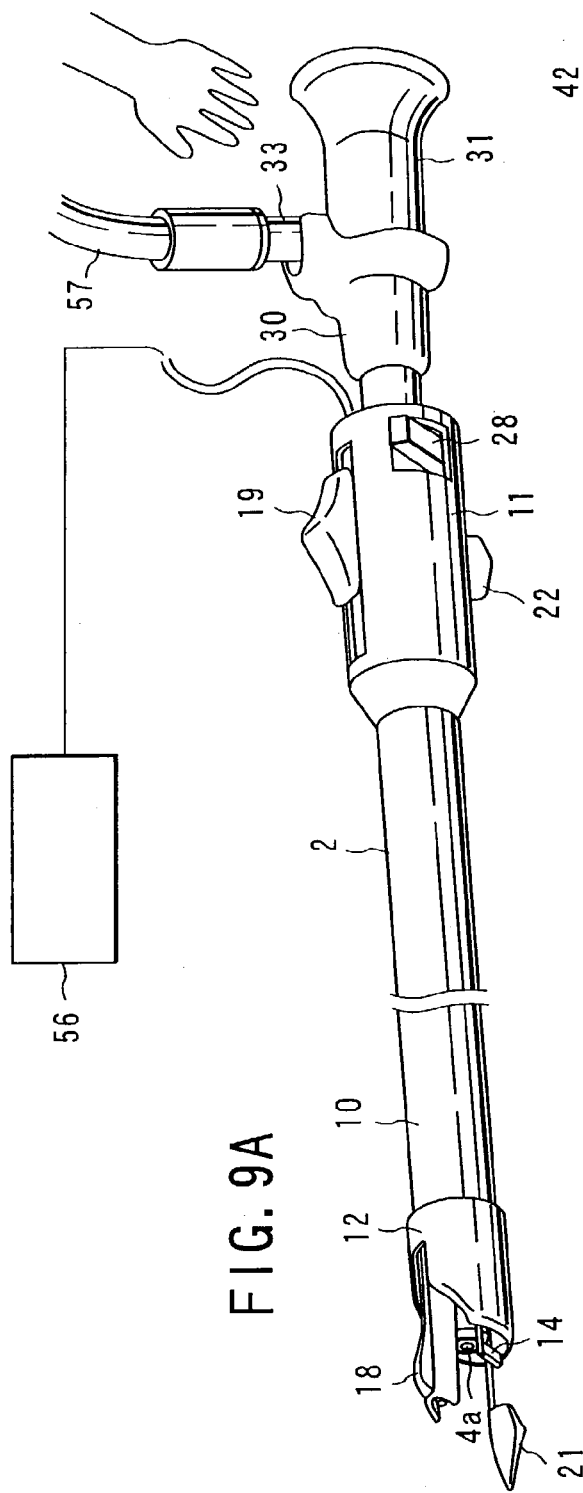
FIG. 9A is a perspective view of a blood vessel harvesting apparatus.
Figure 9C:
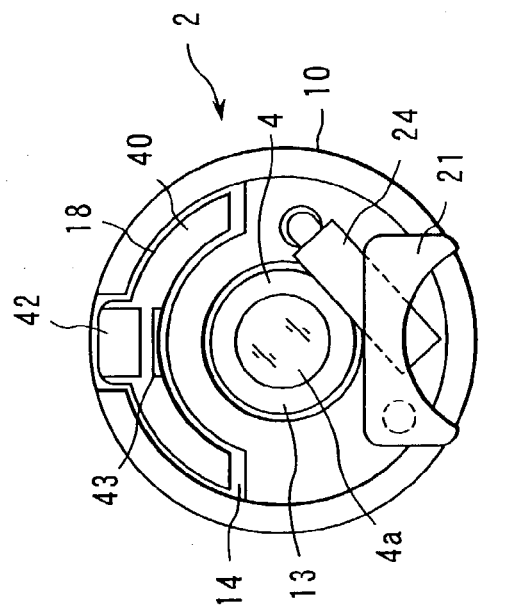
FIG. 9C is a front view of the tip end of the blood vessel harvesting apparatus.
Figure 9B:
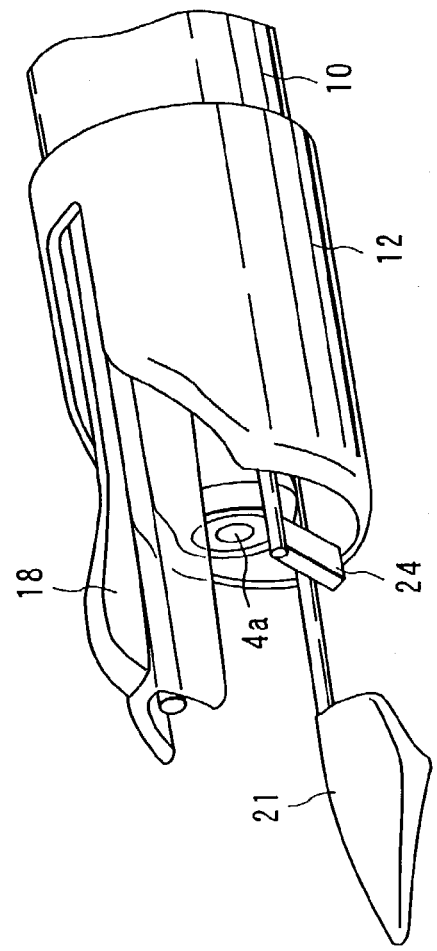
FIG. 9B is a perspective view of a tip end of the blood vessel harvesting apparatus.
Figure 10A:
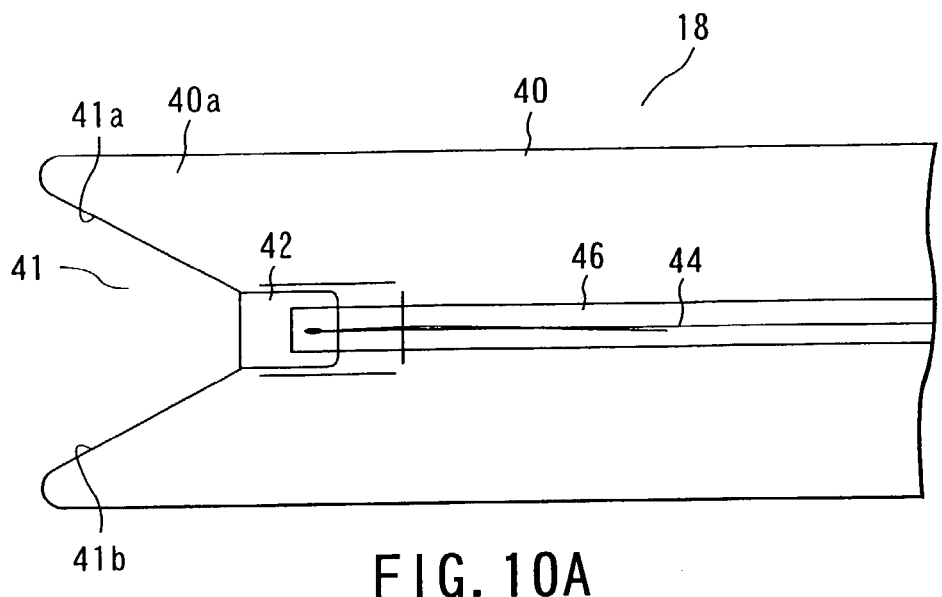
FIG. 10A is a top plan view of a bipolar cutter.
Figure 10B:
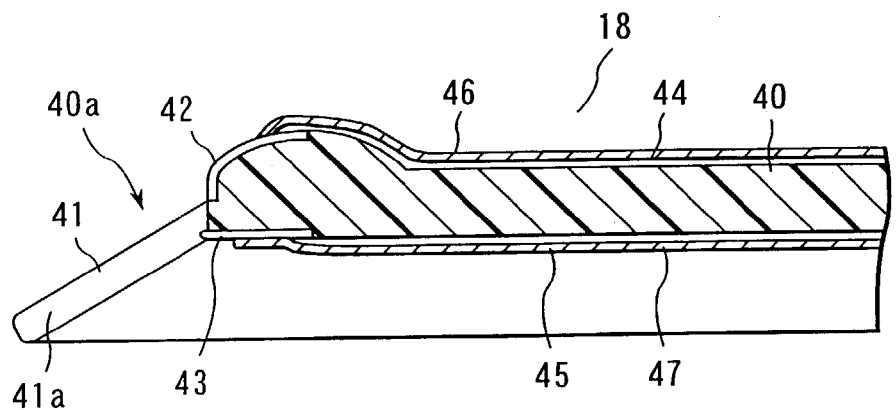
FIG. 10B is a longitudinal sectional side view of the bipolar cutter.
Figure 10C:
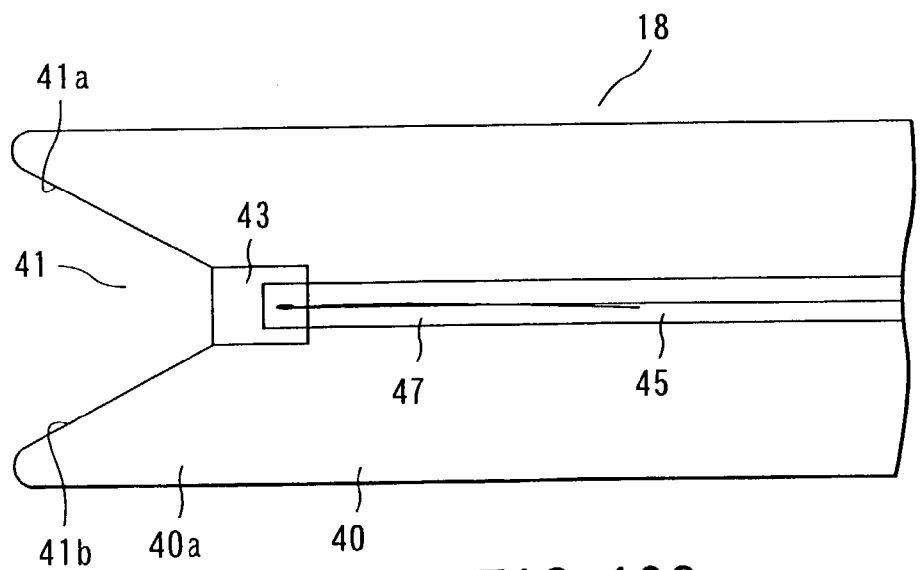
FIG. 10C is a lower surface view of the bipolar cutter.

FIGS. 9A and 9B show that the insertion portion 35 of the rigid endoscope 4 is inserted into the endoscope channel 13 of the treatment sheath 2. In this state, the bipolar cutter 18 and blood vessel holder 21 projects from the tip end of the treatment sheath 2. The bipolar cable 20 is connected to a high-frequency generation apparatus 56, and a light guide cable 57 is connected to the light guide head 33.

Figure 8:
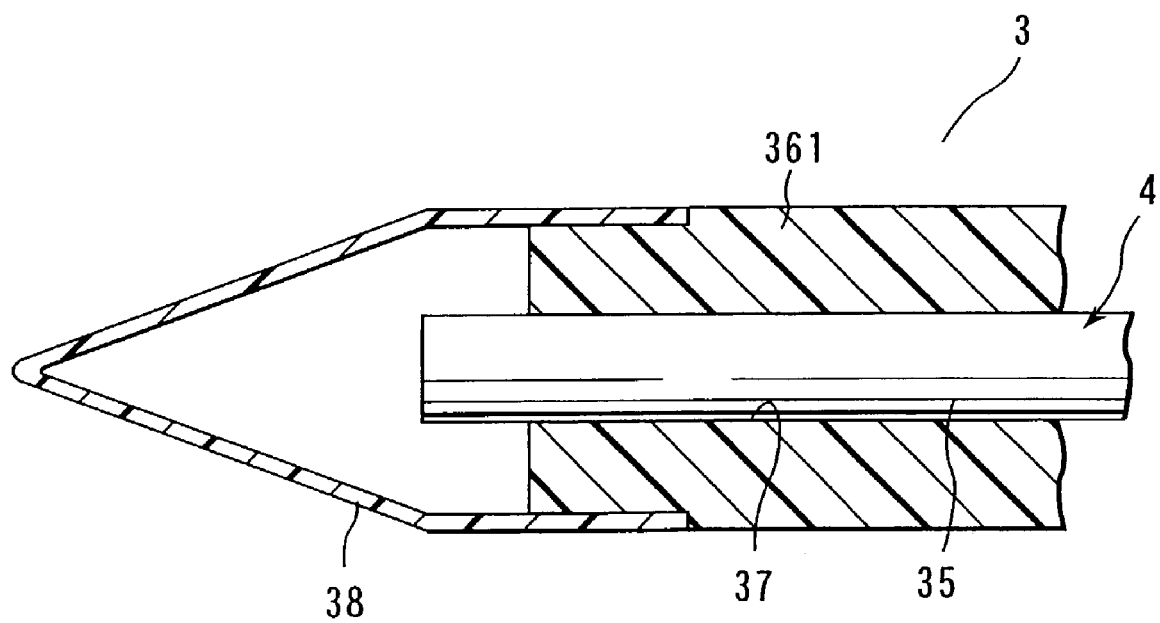
FIG. 8 is a longitudinal sectional side view of the tip end of a dissector.

The dissector 3 will next be described. As shown in FIG. 8, an insertion path 37 for passing through the insertion portion 35 of the rigid endoscope 4 is disposed in the axial center portion of an insertion cylindrical portion 36 which has a straight cylindrical shape. Hydrophilic coating is provided on the surface of the insertion cylindrical portion 36 in order to improve the slip at the insertion time. A stripping member 38 formed in a conical shape by a transparent synthetic resin material is fixed to the distal end of the insertion cylindrical portion 36. An endoscope holding portion 39 is disposed in the proximal end of the insertion cylindrical portion 36 so that the eyepiece portion 31 of the rigid endoscope 4 is held. It is to be noted that the endoscope holding portion 39 preferably includes the same constitution as that of the endoscope holding portion 30 of the treatment sheath 2.

A case will be described in which the blood vessel harvesting apparatus constituted as described above is used to harvest a blood vessel as a harvesting object (hereinafter referred to as the blood vessel) such as a great saphenous vein extending over the whole length including a inguinal portion A of a thigh of a leg and an ankle. The blood vessel thus harvested can be used as a graft blood vessel in, for example, bypass transplantation for the coronary artery.

Figure 14:
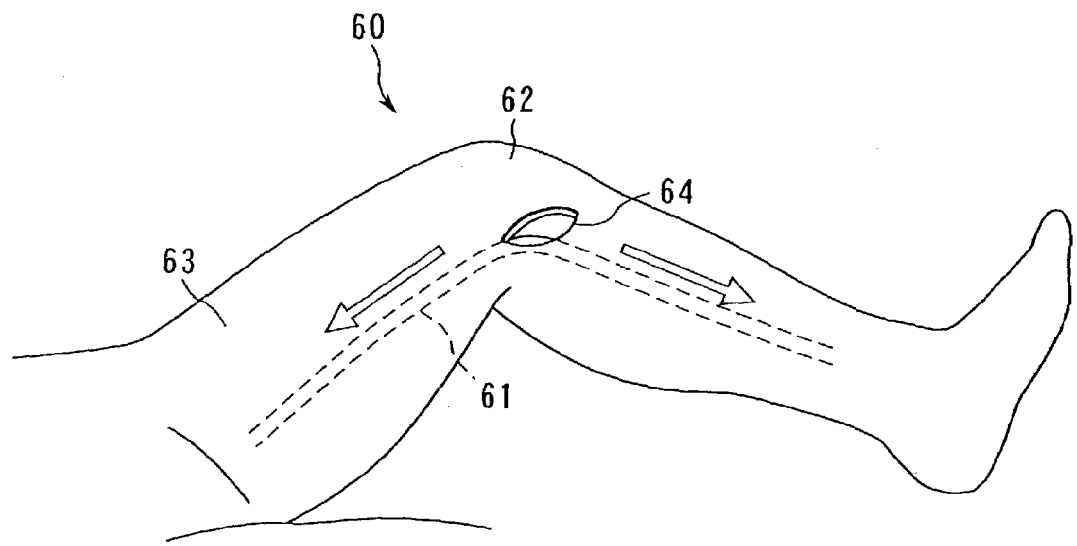
FIG. 14 is a diagram of a state in which a cut skin portion is formed in a leg.

FIG. 14 shows a leg 60 and blood vessel 61. First, when the blood vessel 61 between a knee 62 and inguinal portion 63 is harvested, a cut skin portion 64 is made in one portion of the knee 62 right above the blood vessel 61 by a scalpel.

Subsequently, the blood vessel 61 is exposed in the cut skin portion 64 by a forceps. Furthermore, a tissue right above the blood vessel 61 is stripped by a distance which can be observed through the cut skin portion 64 with the naked eyes with a similar forceps.

Figure 15:
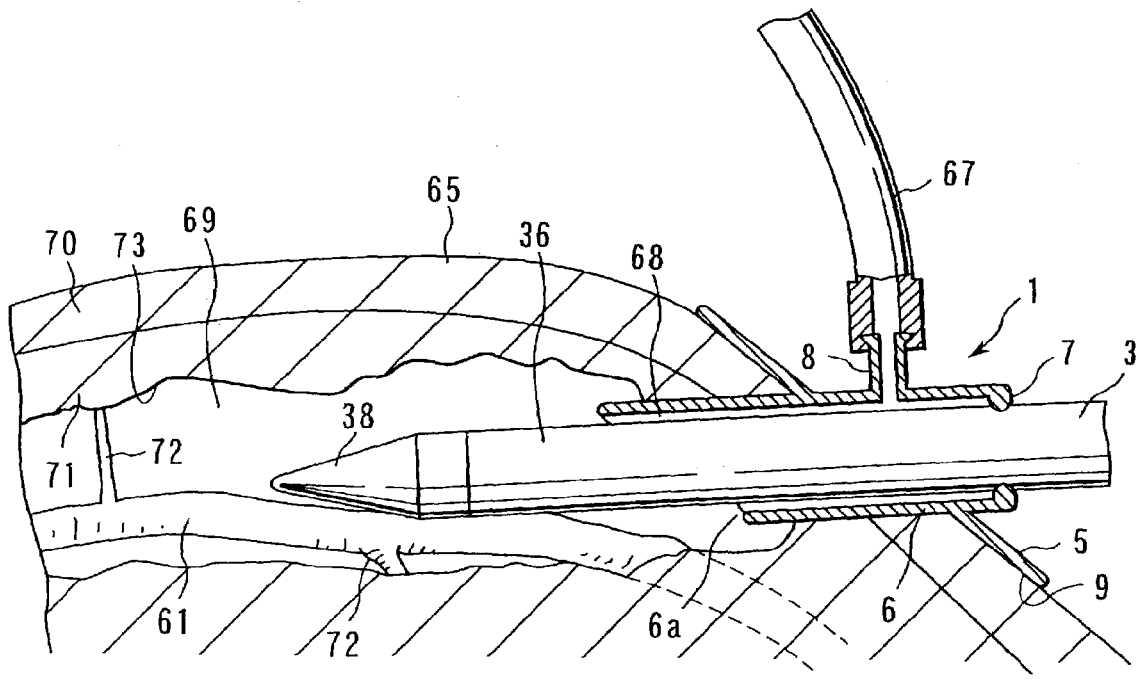
FIG. 15 is a sectional view of a state in which the trocar is attached to the cut skin portion of the leg and the trocar is used as a guide to insert the dissector into a cavity.

Subsequently, the rigid endoscope 4 is inserted into the dissector 3. The endoscope 4 is thereby held in the endoscope holding portion 39 and secured to the light guide head 33. The stripping member 38 is passed is photographed by a TV camera 75 coupled to a TV camera head 74 that is connected to the eyepiece portion 31 of the rigid endoscope 4 inserted in the insertion cylindrical portion 36. A monitor 76 displays the image of the member 38 thus photographed. As shown in FIG. 15, the stripping member 38 is inserted along the blood vessel 61. Where the member is little inserted, the guide tube 6 of the trocar 1 is obliquely inserted toward the inguinal portion 63 (substantially in parallel to the blood vessel 61, the tip end 6a is turned downwards, and the adhesive layer 9 in the lower surface of the flange 5 is bonded/fixed to a scurf skin 65. In this state, an air supply tube 67 connected to an air supply pump 66 is connected to the air supply head 8.

In this case, since the outer peripheral surface of the insertion cylindrical portion 36 is closely attached to the airtight ring portion 7, the inside of the guide tube 6 and cavity 69 is brought into an airtight state, and an air supply path 68 is secured between the guide tube 6 and insertion cylindrical portion 36.

The light guide head 33 of the rigid endoscope 4 is connected to a light source apparatus 78 via the light guide cable 57. Therefore, the cavity 69 can be irradiated and illuminated with an illuminating light from the tip end of the rigid endoscope 4. When the air supply pump 66 is driven, air is supplied into the cavity 69 via the air supply tube 67, air supply head 8, and air supply path 68, and the cavity 69 is expanded. At this time, since the insertion cylindrical portion 36 of the dissector 3 adheres to the airtight ring 7, gas does not leak to the outside, and the cavity 69 can therefore securely be expanded.

Figure 17:
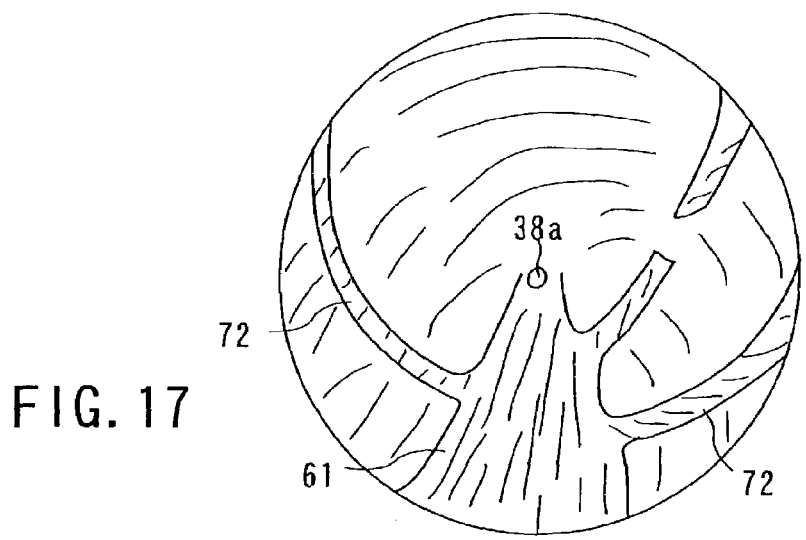
FIG. 17 is a diagram showing a monitor image.

A subcutaneous tissue 70 as a lower layer of the scurf skin 65 and connective tissue on the blood vessel 71 exist in the cavity 69. Moreover, the blood vessel 61 exists in the lower part of the connective tissue on the blood vessel 71, a plurality of side branches 72 are branched from the blood vessel 61, and the other ends of the side branches 72 are connected to the connective tissue on the blood vessel 71. Moreover, a subcutaneous fat 73 is attached to the connective tissue on the blood vessel 71. At this time, when the monitor image is checked, the image is displayed as shown in FIG. 17. The operator can clearly observe the blood vessel 61 and side branches 72 by the monitor 76. It is to be noted that a reference numeral 38a in FIG. 17 denotes the image of the tip end of the stripping member 38 of the dissector 3.

In this way, during the inserting of the dissector 3, in a state in which the cavity 69 is observed by the monitor 76, the connective tissue on the blood vessel 71, blood vessel 61, and side branches 72 are stripped by the stripping member 38 without damaging the side branches 72, and the stripping member 38 is gradually moved forwards by an operation comprising: little pushing inwards; or little returning the member 38. At this time, even when the dissector 3 is vertically/transversely swung, the trocar 1 is not detached from the scurf skin 65. This is because the trocar 1 is fixed to the scurf skin 65 by the adhesive layer 9. In this manner, the dissector 3 is moved from the knee 62 toward the inguinal portion 63 along the blood vessel 61.

The operation described above is repeated several times on the tissue surrounding the blood vessel so that the blood vessel may be peeled off at the harvesting region.

Figure 16:
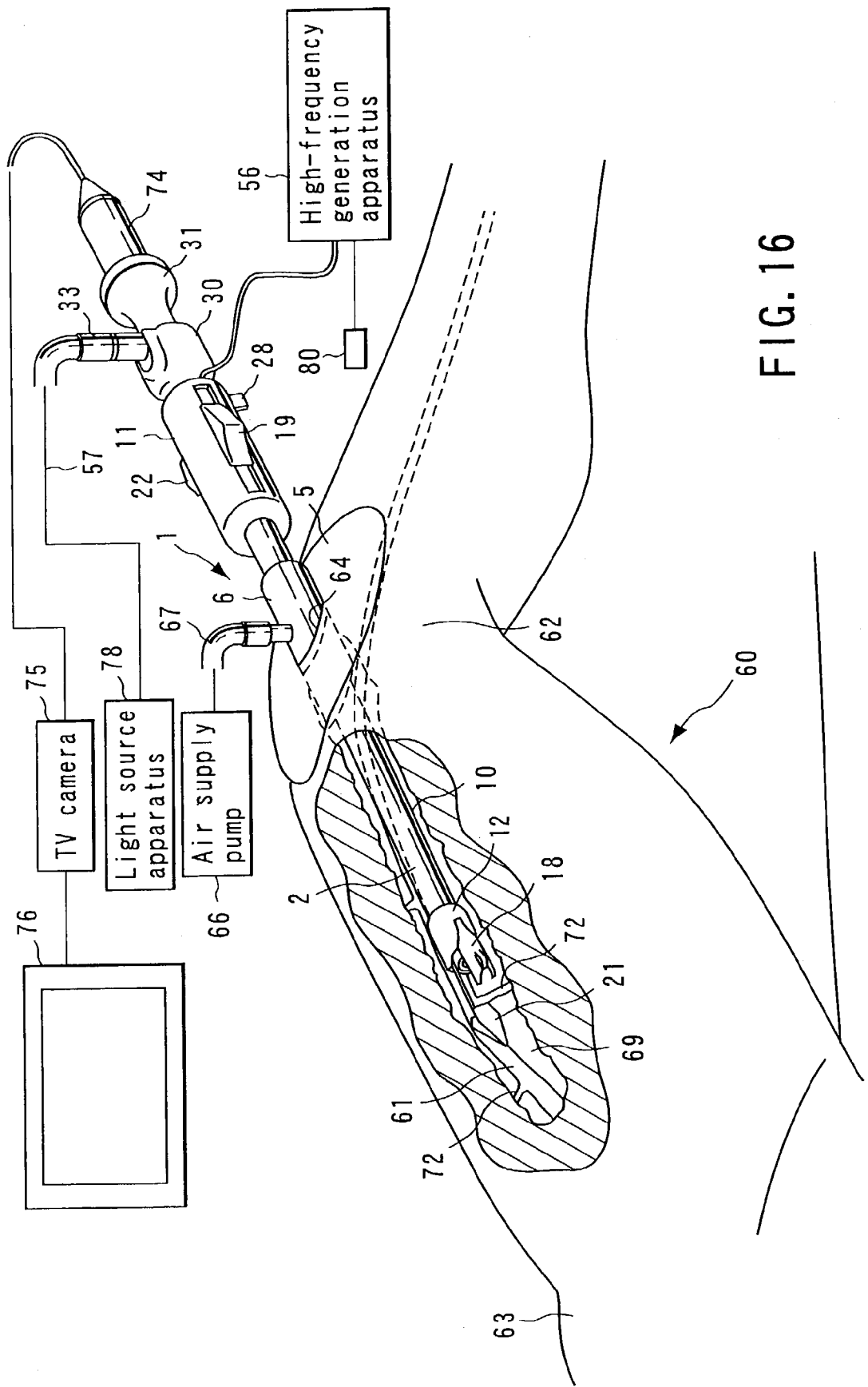
FIG. 16 is a whole constitution diagram of a state in which the trocar is used as the guide to insert the treatment sheath into the cavity.

When a manual stripping operation is completed by using the dissector 3, the dissector 3 is extracted from the trocar 1. The rigid endoscope 4 is detached from the dissector 3. As shown in FIG. 16, the endoscope 4 is inserted into the treatment sheath 2. The sheath 2 holding the rigid endoscope 4 is inserted into the guide tube 6 of the trocar 1. The operation then goes to a treatment step.

In the treatment step, air is applied from the air supply pump 66. The dissector 3 holds the tissue scraped. The treatment is performed in the view field of the endoscope, by using treatment sheath 2 inserted.

While the operation portion cover 11 of the treatment sheath 2 is grasped with operator's one hand, for example, the holder operation portion 22 is moved forwards with the operator's thumb, and the blood vessel holder 21 then projects from the tip end cover 12 of the sheath main unit 10. Moreover, the cutter operation portion 19 is moved forwards with the index finger of the hand in which the operation portion cover 11 is held, and the bipolar cutter 18 then projects from the tip end cover 12. That is, while the operator holds the operation portion cover 11 with one hand, the operator can move the blood vessel holder 21 or bipolar cutter 18 forwards/backwards.

Figure 18:
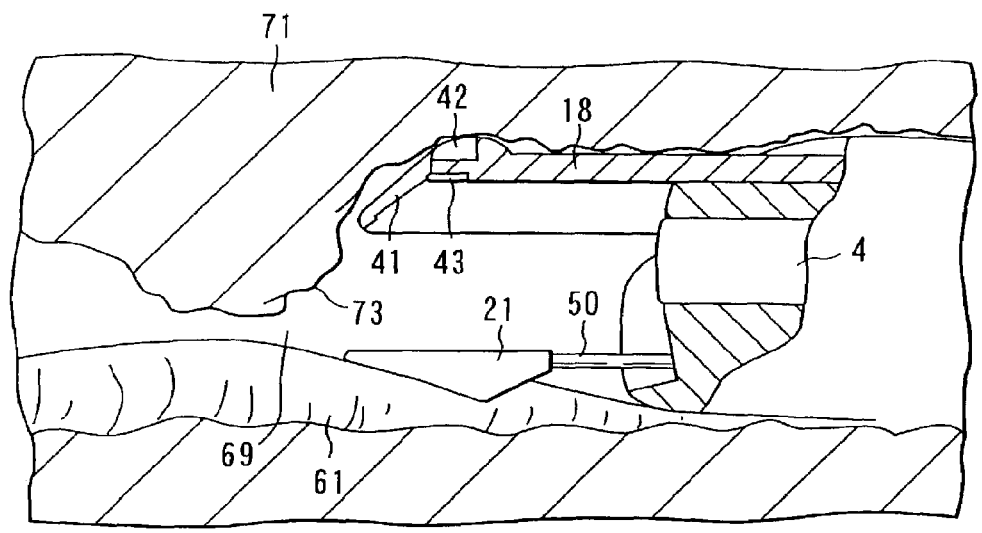
FIG. 18 is a sectional view of the state in which the treatment sheath is inserted in the cavity.

Therefore, as shown in FIG. 18, when a large amount of subcutaneous fat 73 exists in the connective tissue on the blood vessel 71 of the cavity 69, the treatment sheath 2 is pushed forwards to expand the cavity 69 in a projected state of the bipolar cutter 18. At this time, the bipolar cutter 18 prevents the tissue from sagging downwards (presses/discharges the fat tissue in the body cavity) by the curved shape (roof shape) of the cutter main unit 40, so that the view field of the rigid endoscope 4 can satisfactorily be secured. Also, at this time, since the lower surface of the blood vessel holder 21 is formed in the arc concave 49, the holder can be slid and moved forwards on the upper surface of the blood vessel 61, and the blood vessel 61 is not stopped from being damaged.

Figure 19:
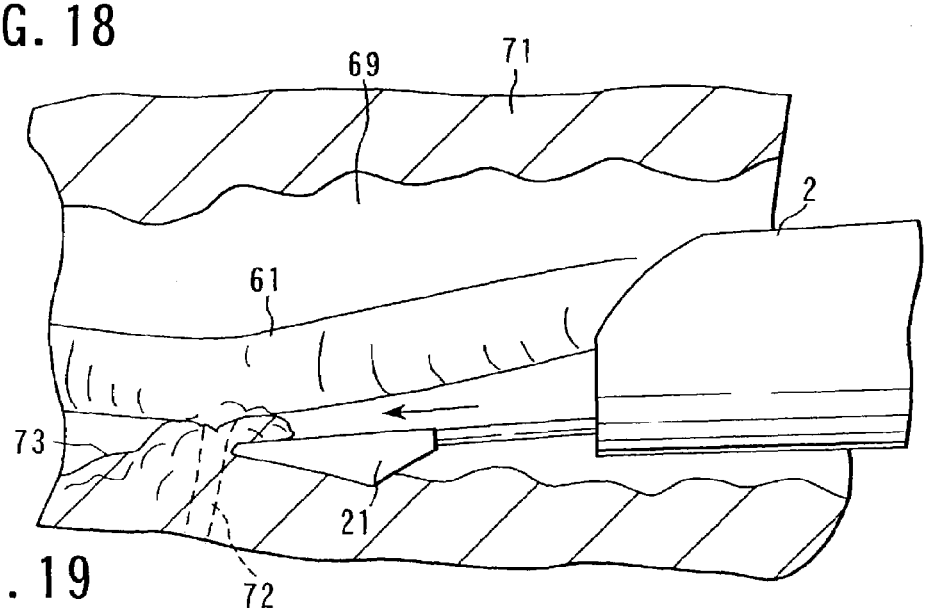
FIG. 19 is a sectional view of a treatment state in the cavity.

As shown in FIG. 19, the side branches 72 are buried in the subcutaneous fat 73 in some case. In this case, the blood vessel holder 21 is projected from the treatment sheath 2, and the stripping portion 51 of the blood vessel holder 21 is pressed onto the subcutaneous fat 73 to strip the subcutaneous fat 73 from the blood vessel 61 or the side branch 71. When the whole treatment sheath 2 is rotated in the peripheral direction in the guide tube 6 of the trocar 1, the blood vessel holder 21 can be rotated to exfoliate the subcutaneous fat 73 from the side branch 72. Since this state is displayed as the monitor image in the monitor 76 as shown in FIG. 20, the operator can confirm the posture of the blood vessel holder 21 by the monitor image, and the blood vessel 61 and side branch 72 are prevented from being damaged.

While the subcutaneous fat 73 of the cavity 69 is removed, the treatment sheath 2 is pushed into the cavity 69, and the blood vessel holder 21 is allowed to approach the side branch 72 as a target. Also in this case, the arc concave 49 is brought in contact with the upper surface of the blood vessel 61, the holder is slid on the upper surface of the blood vessel 61 and can be moved forwards, and the blood vessel 61 is prevented from being damaged.

FIGS. 21A to 21C show a manual operation of holding the side branch 72 by the blood vessel holder 21. The blood vessel holder 21 has the first taper surface 52a, and this surface is continued to the second taper surface 54, the blood vessel holder 21 is moved forwards, and the side branch 72 first is brought in contact with the first taper surface 52a (see FIG. 21B).

When the blood vessel holder 21 is further moved forwards, the side branch 72 contacts the second taper surface 52b from the first taper surface 52a falls, sliding on the hook portion 55, and caught by the hook portion 55 (see FIG. 21C). That is, the first taper surface 52a (or the second taper surface 52b) can allow the blood vessel holder 21 to contact the side branch 72, escape from the side branch 72, and easily move ahead of the side branch 72 (side opposite to the view field with respect to the side branch 72). Moreover, the third taper surface 59 also largely contributes to the ease of forward movement of the blood vessel holder 21. That is, because of the presence of the third taper surface 59, the blood vessel holder 21 can smoothly move forwards without being caught by the tissue which exists below. Therefore, the side branch 72 can easily be held by the forward operation of the blood vessel holder 21.

Figure 22:
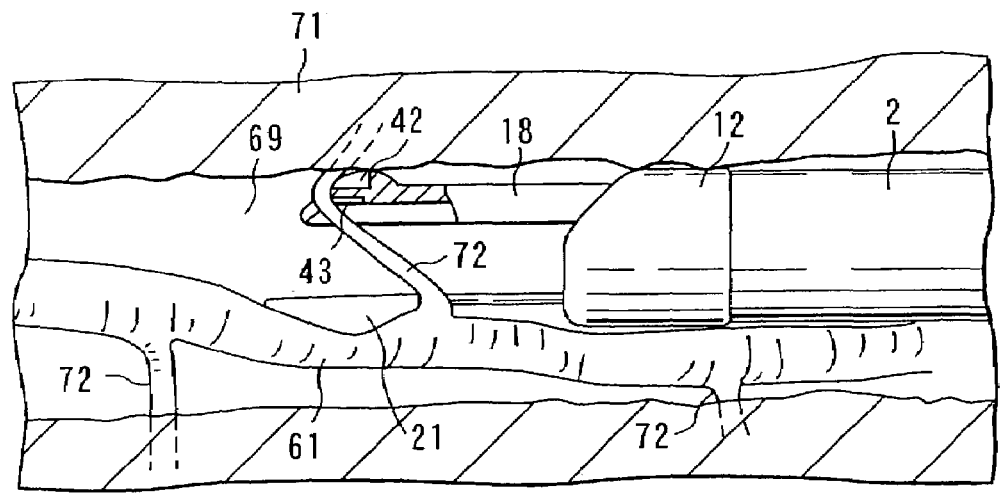
FIG. 22 is a sectional view inside the body in the treatment state.

When the middle of the side branch 72 is hooked on the hook portion 55 of the blood vessel holder 21 and the blood vessel holder 21 is drawn on the hand side (at this time, for example, the hook portion 55 is relatively moved with respect to the bipolar cutter 18), tension is applied to the side branch 72 as shown in FIG. 22. At this time, the blood vessel holder 21 can smoothly move toward the hand side without being caught by the tissue disposed below because of the presence of the fourth taper surface 58. Since one operation rod 50 is connected to the blood vessel holder 21 at this time, and the observation view field is satisfactory. The operation rod 50 is connected to the position eccentric from the center axis of the blood vessel holder 21, and the operation rod 50 lies right above the blood vessel 61. This broadens the observation view further. Therefore, the running of the blood vessel C can easily and clearly be conformed. Hence, the blood vessel holder 21 can hold the side branch 72 more readily and firmly. As a result, it is easy to apply the tension to the side branch 72. Particularly, if the blood vessel holder 21 is formed of the transparent material, the visibility of the blood vessel and tissue can further be improved (therefore, in another preferred embodiment of the present invention, the blood vessel holder 21 is formed by the transparent material).

Figure 23:
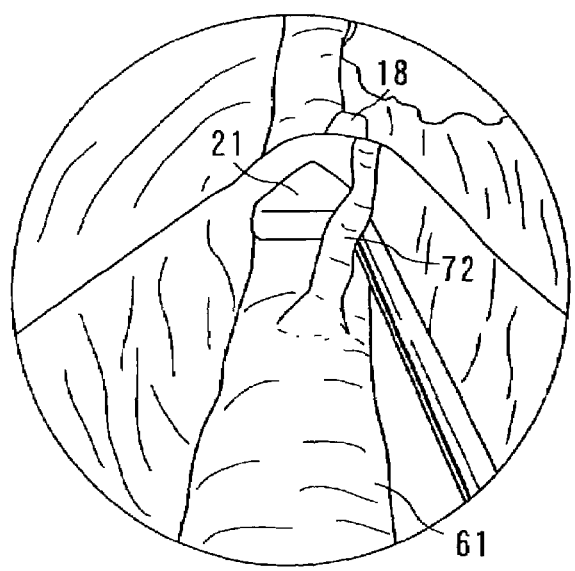
FIG. 23 is a diagram showing the monitor image.

FIG. 23 shows the monitor image in which the side branch 72 is hooked on the hook portion 55 of the blood vessel holder 21. An operator can check by this monitor image that the side branch 72 has been held. When the side branch 72 is held by the blood vessel holder 21 not on the hand side, but on the opposite side of the side branch 72, the side branch 72 is positioned on the hand side of the observation view field, and the periphery of the side branch 72 can clearly be confirmed by the rigid endoscope 4 (when the blood vessel holder 21 is disposed on the hand side of the side branch 72, the blood vessel holder 21 obstructs the front observation view field, and the positional states of the side branch 72 and blood vessel 61 cannot satisfactorily be confirmed). Therefore, as described later, the side branch 72 can safely be cut without damaging the blood vessel 61.

When the state shown in FIG. 23 is formed, next the bipolar cutter 18 is moved forwards (the bipolar cutter 18 is relatively moved with respect to the hook portion 55) and approaching the side branch 72 held by the blood vessel holder 21. The hook portion 55 of the holder 21 may not be used, depending upon the position that the side branch assumes. Rather, the side branch may be held at a position away from the hook portion 55. In this case, the blood vessel 61 can be held in the arc concave 49. Further, as seen from the monitor image of FIG. 24, the blood vessel 61 can be moved backwards from the bipolar cutter 18 by using the blood vessel holder 21, preventing the bipolar cutter 18 from contacting the blood vessel 61. This operation can easily be achieved by disposing the bipolar cutter 18 opposite to the blood vessel holder 21 as described above. By this arrangement, a predetermined distance can securely be kept between the incised/treated portion of the side branch 72 and the blood vessel 61, the side branch 72 is incised by the bipolar cutter 18 in the position apart from the blood vessel 61, and the blood vessel 61 can be prevented from being damaged. When the predetermined distance can be kept between the incised/treated portion of the side branch 72 and the blood vessel 61 in this manner, a knot margin can be secured in binding the cut portion of the side branch 72 left on the blood vessel 61 side with a ligature or the like, after the side branch 72 is cut and the blood vessel 61 is extracted. This constitution is therefore useful.

Figure 24:
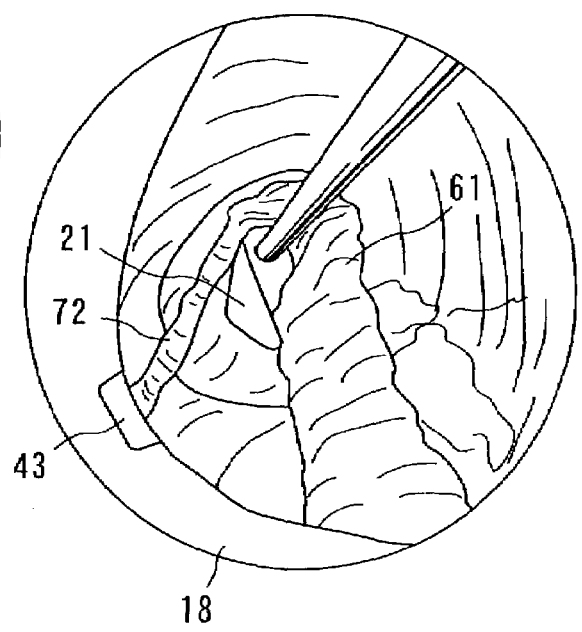
FIG. 24 is a diagram showing the monitor image.

As seen from the monitored image shown in FIG. 24, the hook portion 55 of the blood vessel holder 21 may not used, depending upon the positions that the blood vessel 61 and the side branch 72 take. Instead, the other part of the holder 21, located outside the portion 55, may be used to hold the side branch, In this case, the holder 21 can hold the blood vessel at its concave surface 49. Thus, the blood vessel 61 can be moved away from the bipolar cutter 18 by using the blood vessel holder 21, in order to prevent the cutter 18 from contacting the blood vessel 61.

FIGS. 25A to 25C show a manual operation of cutting the side branch 72 by the bipolar cutter 18. Since the V groove 41 is formed in the tip end of the bipolar cutter 18, and when the bipolar cutter 18 is moved towards the side branch 72, the side branch 72 is drawn toward the bottom of the V groove 41. Therefore, as shown in FIG. 26A, the side branch 72 contacts the cut electrode 43, and the body-side electrode 42 contacts the connective tissue on the blood vessel 71 or side branch 72. That is, in the bipolar cutter 18 according to the present embodiment, the side branch 72 can be guided into the electrodes 42, 43 substantially positioned in the intersection of the respective sides 41a, 41b by the wall surfaces of the V groove 41 corresponding to the respective sides 41a, 41b which form the V shape.

After confirming by the monitor image that the side branch 72 contacts the cut electrode 43 and the body-side electrode 42 contacts the connective tissue on the blood vessel 71 or side branch 72, the operator operates a foot switch 80 of the high-frequency generation apparatus 56 to supply a high-frequency current. The body-side electrode 42 contacts the blood vessel connecting tissue or the side branch 72 at a larger area than the cut electrode 43 contacts the tissue or the side branch 72. This means that the current density is higher in the cut electrode 43 than in the body-side electrode 42. Hence, the cut electrode 43 can cut the tissue efficiently. Then a region in contact with the body-side electrode 42 of the connective tissue on the blood vessel 71 or side branch 72 is coagulated, and the side branch 72 is cut by the cut electrode 43. That is, as FIG. 26B shows, the portion of the blood vessel 61 connected to the connective tissue on the blood vessel 71 by the side branch 72 is cut off by cutting the side branch 72. At this time, since the body-side electrode 42 having the large contact area is disposed on the upper side (body side) farther from the blood vessel 61 than the cut electrode 43, the thermal influence on the blood vessel 61 is minimized.

Since the bipolar cutter 18 is just pressed onto the blood vessel in this manner, the blood vessel can be cut. That is, operation other than the forward/backward movement is not required in cutting the blood vessel. Therefore, operability is enhanced.

Figure 28:
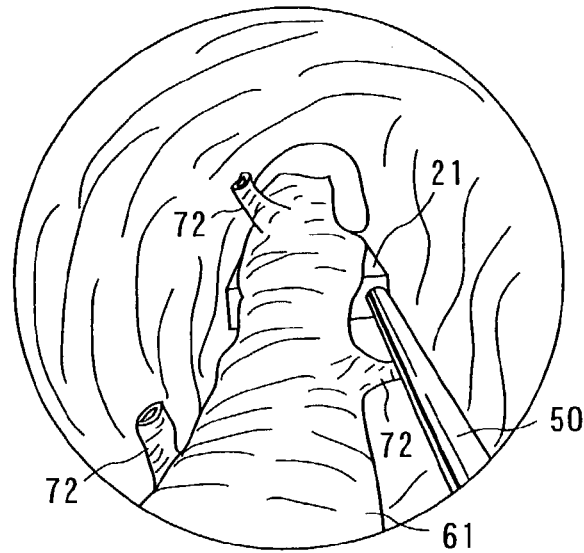
FIG. 28 is a diagram showing the monitor image.

When the side branch 72 is cut as described above, as shown in FIG. 27, the blood vessel holder 21 is passed under the blood vessel 61 to lift up the blood vessel. It is confirmed by the monitor image shown in FIG. 28 whether or not the side branch 72 is completely cut/treated.

The treatment sheath 2 is further pushed forwards in the cavity 69. While observing the monitored image of the cavity 69, the surgeon may move the blood vessel holder 21 toward the next side branch 72. The surgeon repeats the above-mentioned manual operation, using the bipolar cutter 18, on all side branches 72. The blood vessel 61 is thereby cut completely from the connective tissue on the blood vessel 71.

Figure 29:
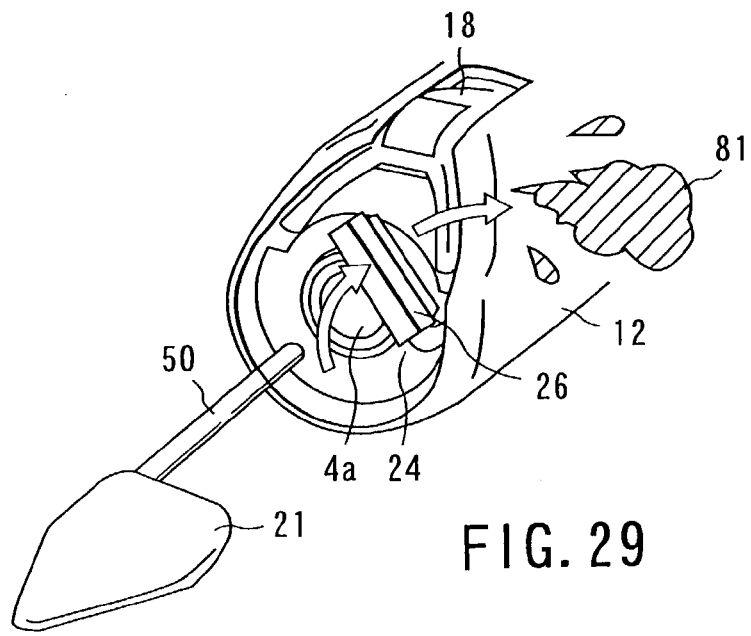
FIG. 29 is a perspective view of the tip end of the treatment sheath.

When the method of cutting the side branch 72 is repeated in this manner, the foreign materials 81 such as blood, mucosa, and subcutaneous fat 73 adhere to the objective lens surface 4a of the rigid endoscope 4, and the view field by the rigid endoscope 4 is sometimes obstructed. In this case, while the operation portion cover 11 remains to be grasped, and when the wiper operation portion 28 is manually rotated against an urging force of the torsion coil spring 29, as shown in FIG. 29, the wiper 24 rotates via the wiper rod 25, and the foreign materials 81 such as the blood, mucosa, and subcutaneous fat 73 sticking to the objective lens surface 4a can be scraped away by the scraping portion 26a of the wiper rubber 26.

The wiper 24 is urged by the torsion coil spring 29. When the wiper operation portion 28 is released from the fingers, the wiper is returned in a retreat direction from the objective lens surface 4a. Therefore, when the above-described operation is repeated several times, even the foreign materials 81 such as the subcutaneous fat 73 adhering to and not easily dropping from the objective lens surface 4a can cleanly be scraped off. Moreover, when the fingers are released from the wiper operation portion 28, the wiper 24 returns, moving a away from the objective lens surface 4a and is still biased. Hence, the wiper 24 would not project, by accident, into the view field. In other words, wiper 24 would not narrow the view field of the rigid endoscope 4.

Moreover, when the cutting of the side branch 72 by the bipolar cutter 18 is repeated, as shown in FIG. 30, the foreign materials 81 such as the mucosa and subcutaneous fat 73 also adhere to the inner surface of the bipolar cutter 18 because of the roof shape of the bipolar cutter 18. However, when the bipolar cutter 18 is moved backwards by the cutter operation portion 19 and drawn into the first treatment device channel 14, the mucosa and subcutaneous fat 73 are scraped off by the front end surface of the sheath main unit 10. Therefore, the foreign materials 81 adhering to the bipolar cutter 18 can easily be scraped off. It is to be noted that in the present embodiment, in order to scrape off the mucosa and subcutaneous fat 73 adhering to the bipolar cutter 18 by the front end surface of the sheath main unit 10, a clearance between the bipolar cutter 18 and sheath main unit 10 (clearance between the outer surface of the bipolar cutter 18 and the inner surface of the first treatment device channel 14) is set to be small.

As shown in FIG. 31, the scraped foreign materials 81 stick to the objective lens surface 4a of the rigid endoscope 4 and sometimes obstruct the view field. Even in this case, when the wiper operation portion 28 is operated to rotate the wiper 24 as described above, the foreign materials 81 sticking to the objective lens surface 4a can be scraped off.

While the operation of scraping off the foreign materials 81 sticking to the bipolar cutter 18 or objective lens surface 4a is repeated, the manual operation of cutting the side branch 72 to cut the blood vessel 61 from the connective tissue on the blood vessel 71 is repeated. When the operation reaches the inguinal portion 63, the cutting of the side branch 72 is terminated. Subsequently, the small incision is formed in the inguinal portion 63 right above the blood vessel 61 with the scalpel. The blood vessel 61 is pulled out through the cut skin portion. The operator can cut the drawn portion of the blood vessel 61, and ligate both cut ends of the blood vessel 61 with a suture.

Subsequently, the harvesting operation of the blood vessel 61 extending toward the ankle from the cut skin portion 64 of the knee 62 is carried out and finally one blood vessel (about 60 cm) is harvested from the cut skin portion 64. The manual operation is basically similar to the manual operation performed on the blood vessel 61 extending to the inguinal portion 63 from the knee 62, and the description thereof is omitted. The vessel which is cut on its both sides is removed from the cut skin portion 64.

In the method of harvesting the blood vessel 61, a manual operation is performed on the inguinal portion 63, and another manual operation is performed at the ancle. Instead, the blood vessel 61 may be first scraped from the connecting tissue 71 at both the inguinal portion 63 and the ancle. Then, the treatment sheath 2 may be used in place of the dissector 3 when the blood vessel 61 is completely cut from the connecting tissue 71. This reduces the number of times the sheath 2 and the dissector 3 should be exchanged with each other. The manual operation can be more smoothly carried out than otherwise.

As described above, in the bipolar cutter 18 as the treatment device for cutting the living tissue of the present embodiment, the V groove (guide portion) 41 along which the blood vessel is guided into the electrodes 42, 43 with movement of the cutter main unit 40 in an axial direction is formed in the tip-end treatment portion 40a. Therefore, when the cutter main unit 40 is simply moved forwards/backwards, the blood vessel can be approached and simultaneously cut. That is, when the tip-end treatment portion 40a (electrodes 42, 43) is pressed onto the object blood vessel to be cut and electricity is supplied, the blood vessel can be cut. Therefore, without performing further operation of pressing and moving the blade or opening/closing the jaw as in the related art, the blood vessel can be cut (the blood vessel can easily be cut).

Moreover, a pair of electrodes 42, 43 of the bipolar cutter 18 of the present embodiment are different from each other in a contact area in contact with the living tissue, and the living tissue is incised by the electrode 43 which has a small contact area. That is, the contact area of the body-side electrode 42 is larger than that of the cut electrode 43, thereby the electric current concentrates in the cut electrode 43. Thus, the current density is high in the cut electrode 43. The blood vessel can be easily cut (incised), merely by pressing the electrodes 42 and 43 onto the blood vessel (i.e., side branch 72) and passing a current.

Furthermore, in the bipolar cutter 18 of the present embodiment, the body-side electrode 42 having a large contact area is disposed on an upper side (body side) farther from the blood vessel 61 than the cut electrode 43 is. That is, a distance between the body-side electrode 42 having a large contact area and the blood vessel holder 21 is set to be longer than that between the cut electrode 43 having a small contact area and the blood vessel holder 21. When the electrode 42 having the large contact area is disposed to be as distant from the harvested blood vessel 61 as possible, thermal influence on the blood vessel 61 can be minimized. Additionally, after the cutting, the side branch 72 remaining in the body can also be stopped from bleeding.

Figure 32A:
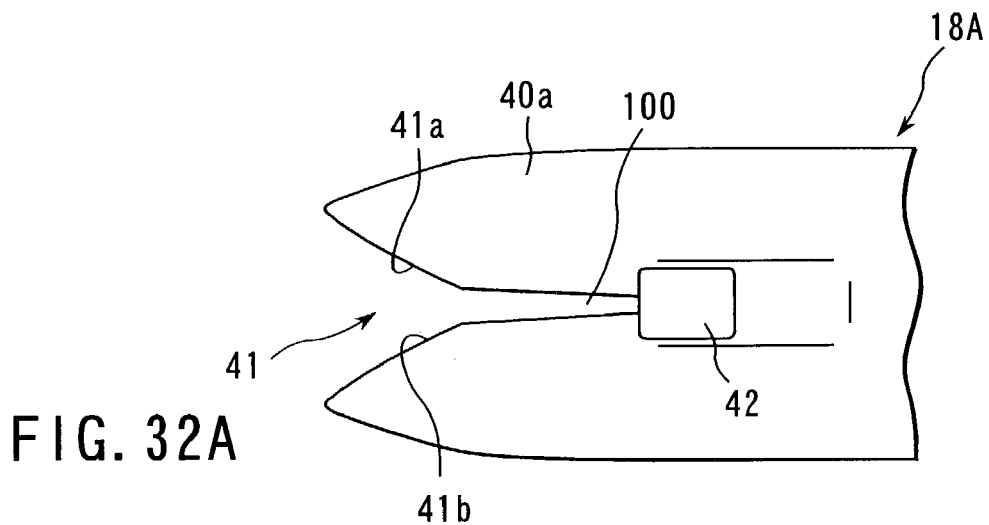
FIG. 32A is a plan view of a tip-end treatment portion of the bipolar cutter according to a first modification example.
Figure 32B:
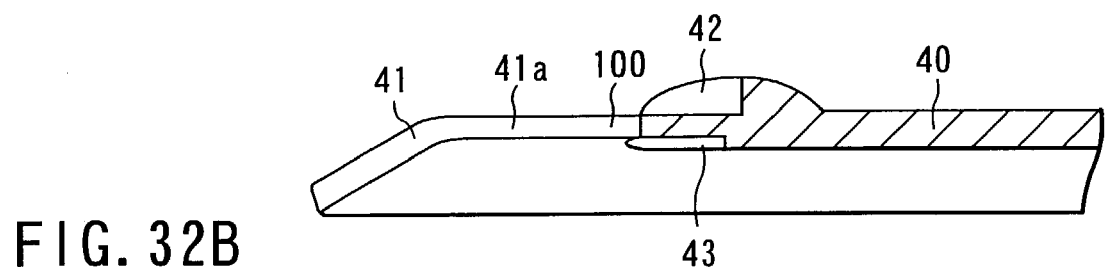
FIG. 32B is a longitudinal sectional side view of the tip-end treatment portion of FIG. 32A.

FIGS. 32A and 32B show a first modification example of the above-described bipolar cutter. For the V groove 41 of a bipolar cutter 18A according to this modification example, a portion on an electrodes 42, 43 side is largely narrowed down. That is, the portion of the V groove 41 on the electrodes 42, 43 side is formed as a restricted groove 100 which has a width smaller than that of the portion on a tip-end opening side of the V groove 41.

Figure 33:
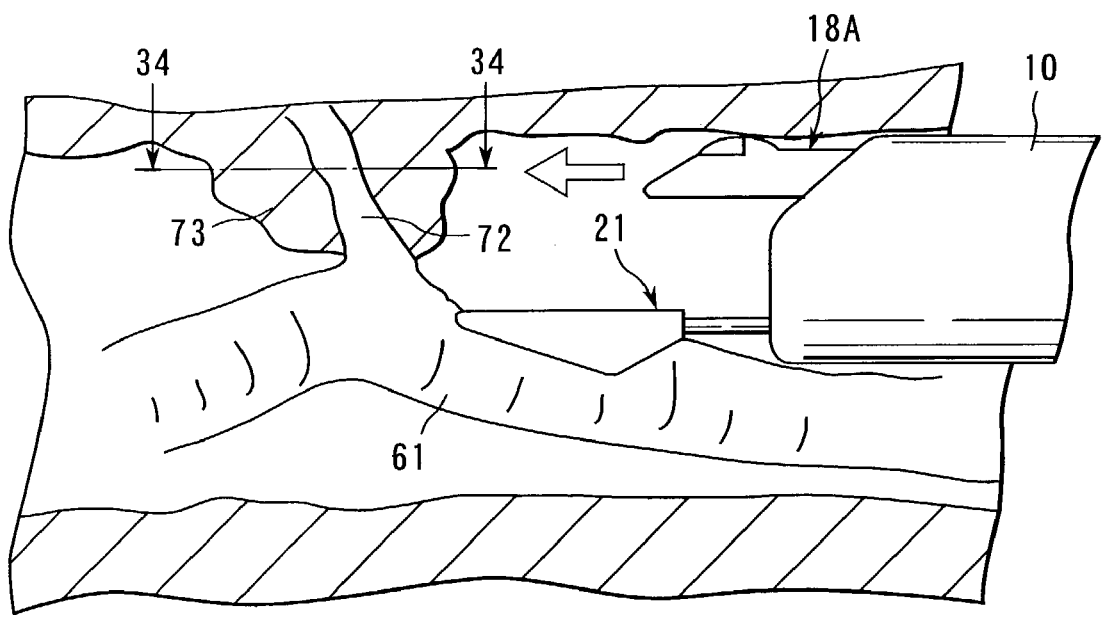
FIG. 33 is a diagram showing a use mode of the bipolar cutter of FIG. 32A.
Figure 34:
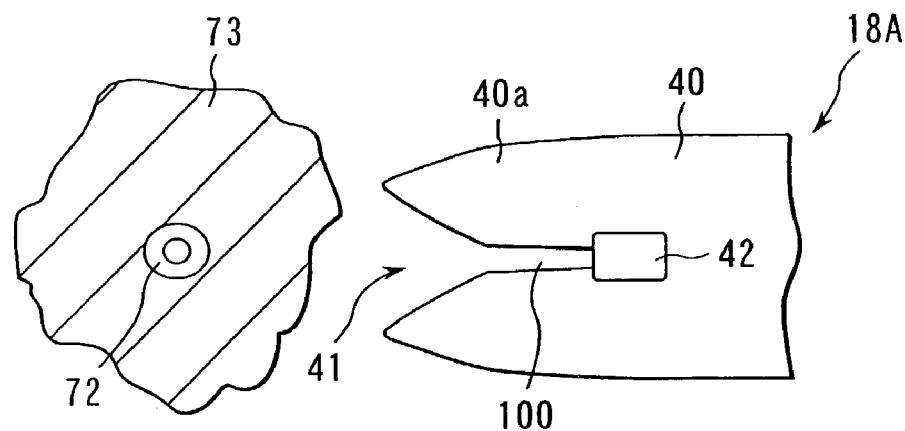
FIG. 34 is a sectional view along a line 34-34 of FIG. 33.
Figure 35:
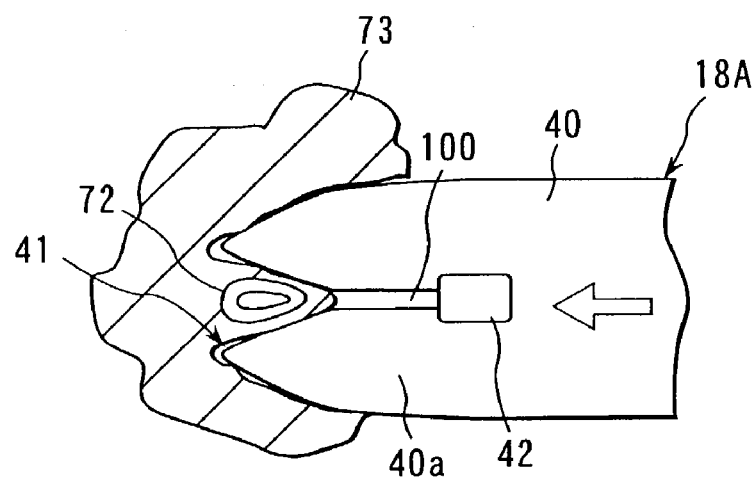
FIG. 35 is a sectional view showing the use mode of the bipolar cutter of FIG. 32A.
Figure 36:
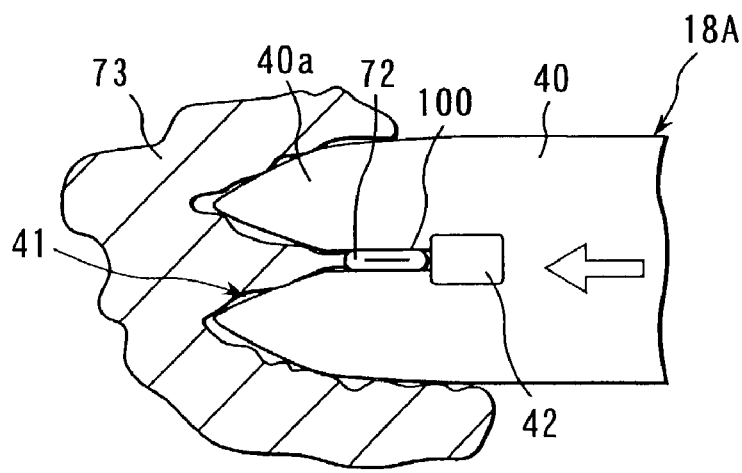
FIG. 36 is a sectional view showing the use mode of the bipolar cutter of FIG. 32A.
Figure 37:
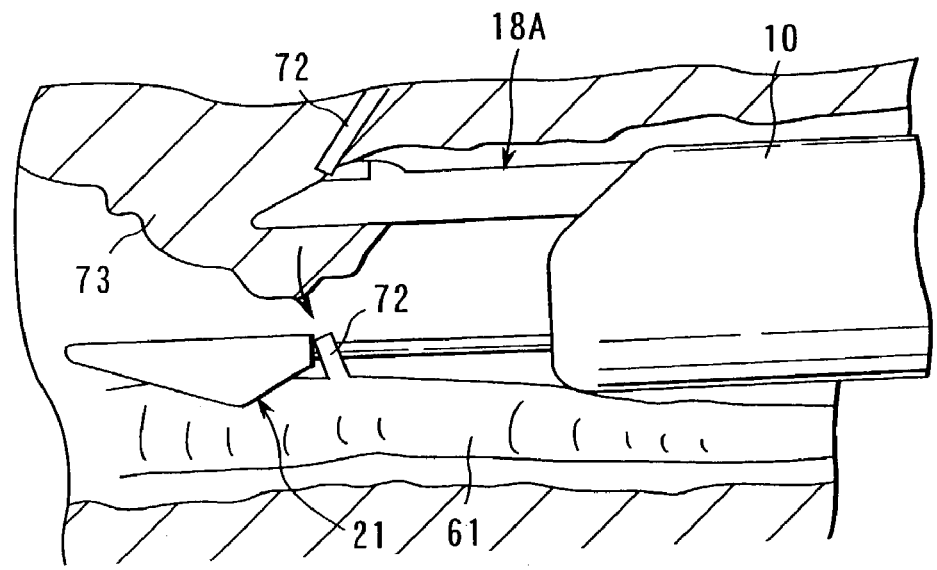
FIG. 37 is a sectional view showing the use mode of the bipolar cutter of FIG. 32A.

In this constitution, as shown in FIGS. 33 and 34, when the side branch 72 is buried in the subcutaneous fat 73, the bipolar cutter 18A is pressed onto the subcutaneous fat 73 to introduce the side branch 72 and the subcutaneous fat 73 around the side branch into the V groove 41. When the bipolar cutter 18A is further pushed forwards from this state of FIG. 35, as shown in FIG. 36, only the side branch 72 can be introduced into the restricted groove 100 having the small width. That is, by this restricted groove 100, the subcutaneous fat 73 is removed from the periphery of the side branch 72, and only the side branch 72 can be brought into contact with the electrodes 42, 43 and cut (see FIG. 37).

Figure 38:
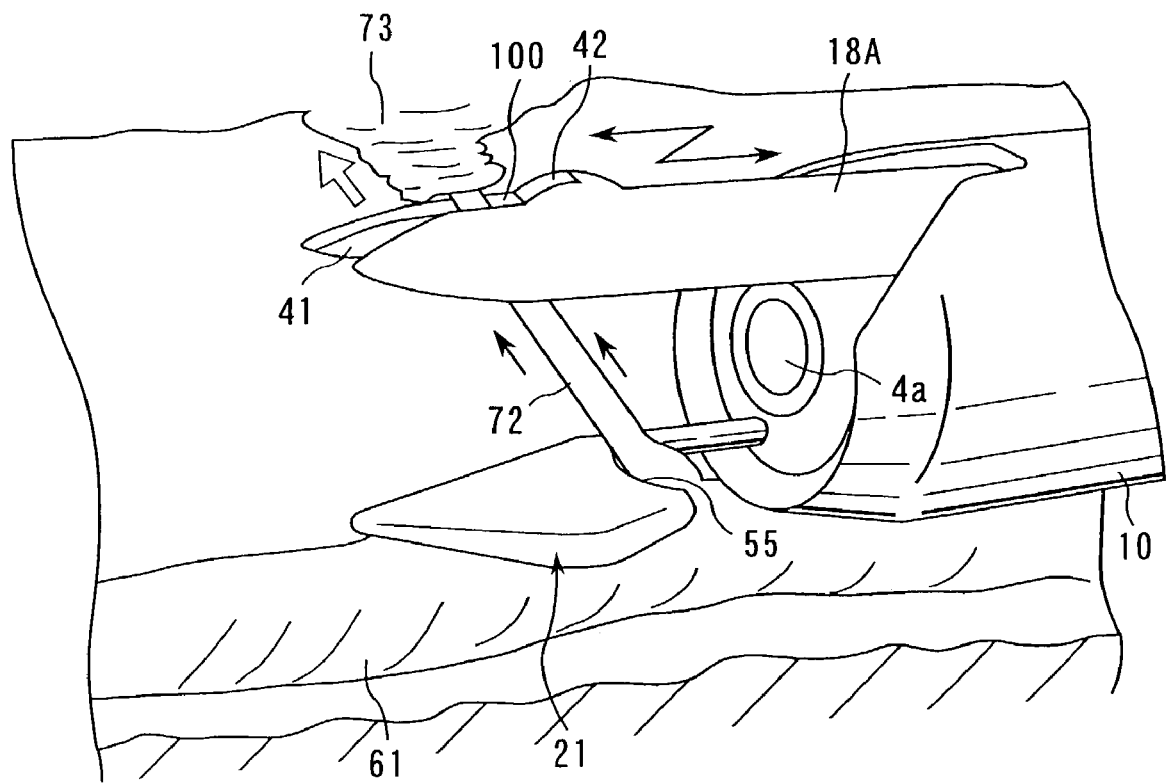
FIG. 38 is a perspective view showing another use mode of the bipolar cutter of FIG. 32A.

FIG. 38 shows another use mode of the restricted groove 100. That is, in the state of FIG. 36, the hook portion 55 of the blood vessel holder 21 is caught in the middle of the side branch 72 to pull the blood vessel holder 21 toward the hand side and tension is applied to the side branch 72. While this state is kept, as shown by arrows in FIG. 38, the bipolar cutter 18A is slightly moved forwards/backwards and slid upwards, and the subcutaneous fat 73 can be stripped from the periphery of the side branch 72 by the restricted groove 100.

FIGS. 39 to 42 show another use mode of the restricted groove 100. In this use mode, the groove width of the restricted groove 100 is set to be smaller than the diameter of the side branch 72. Therefore, as shown in FIGS. 39 to 41, when the side branch 72 is inserted into the restricted groove 100, the side branch 72 is compressed in the restricted groove 100, and finally opposite blood vessel walls of the side branch 72 contact each other (see FIG. 41). Even when electricity is supplied to the electrodes 41, 42, the blood flow in the compressed portion of the side branch remains to be cut off, but the side branch 72 is coagulated/incised, and the cut surface is stopped from bleeding (see FIG. 42). Thus, both cut ends are sealed.

When the groove width of the restricted groove 100 formed in the V groove 41 is set to be smaller than the diameter of the blood vessel as the cutting object in this manner, the blood vessel can be compressed to stop the blood flow, and coagulated/incised. Therefore, it is possible to perform very useful incision/bleeding stop.

It is to be noted that in this case even with the restricted groove 100 as a parallel groove having a uniform groove width over the total length, or the groove having a gradually tapered groove configuration, the equivalent effect is obtained. Moreover, in the manual operation of extracting a saphenous vein, a width L of the restricted groove 100 (see FIG. 39) is preferably 0.3 mm to 0.7 mm.

Figure 43:
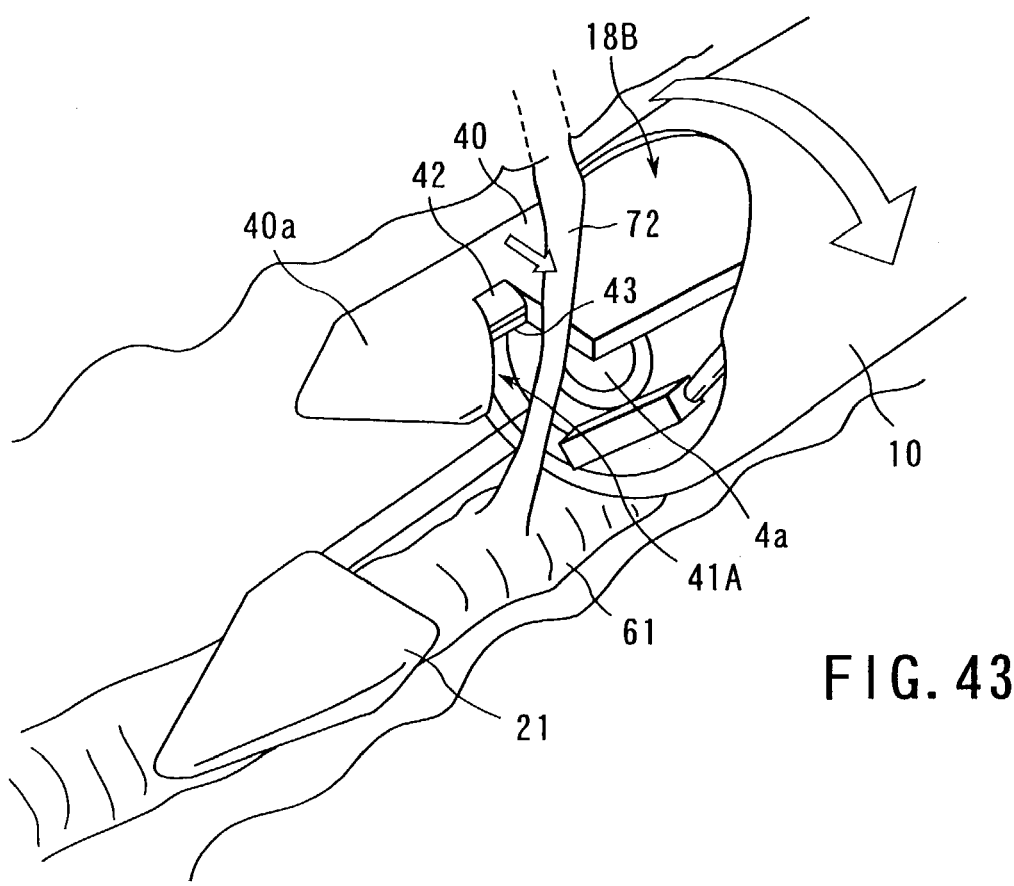
FIG. 43 is a perspective view of the tip end of the blood vessel harvesting apparatus in which the bipolar cutter according to a second modification example is incorporated.

FIG. 43 shows a second modification example of the above-described bipolar cutter. A V groove 41A of a bipolar cutter 18B according to this modification example is formed in a lateral portion of the tip-end treatment portion 40a. In this constitution, the side branch 72 can laterally be approached and cut. In this case, the side branch 72 is introduced into the V groove 41A beside the tip-end treatment portion 40a. When the sheath main unit 10 is rotated in this state as shown by arrows in FIG. 43, the side branch 72 can easily be cut by the electrodes 42, 43. That is, the V groove 41 of the above-described embodiment guides the blood vessel 61 into the electrodes 42, 43 with the movement of the cutter main unit 40 in the axial direction, but the V groove 41A of the present modification example guides the blood vessel 61 into the electrodes 42, 43 with the movement of the cutter main unit 40 in a direction substantially crossing at right angles to the axial direction.

Figure 44:
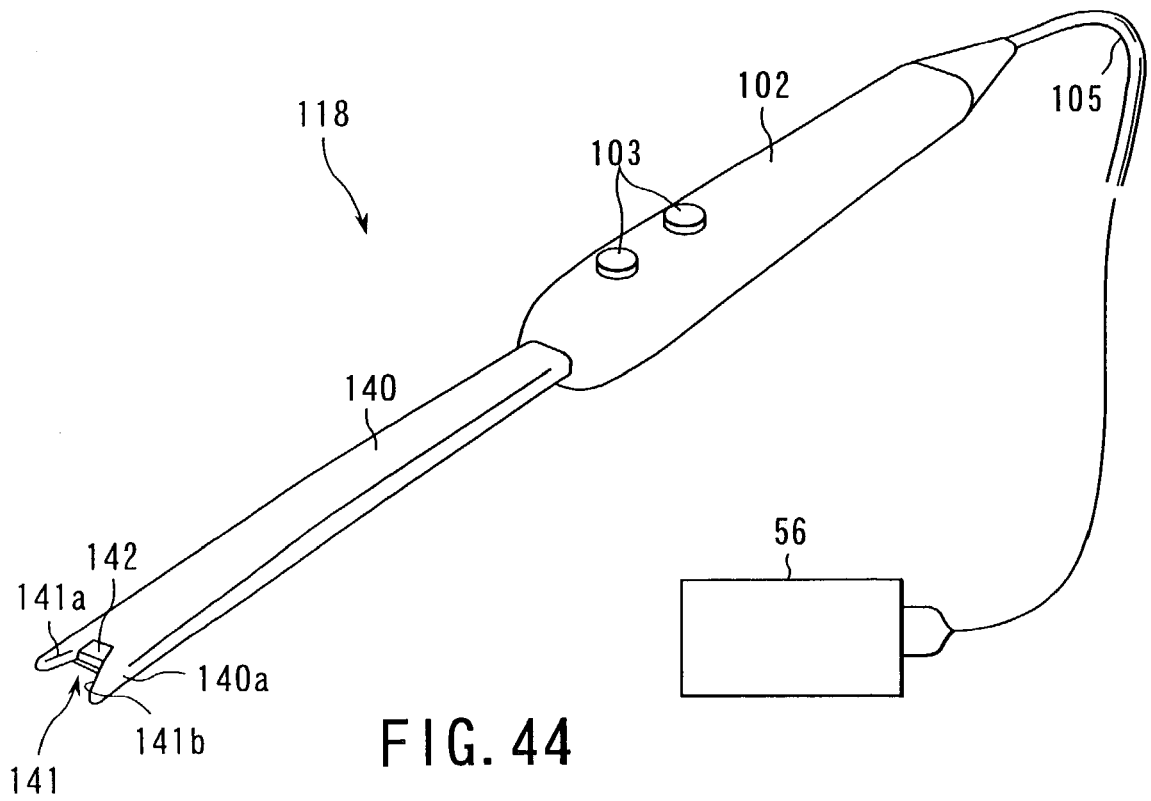
FIG. 44 is a perspective view of the treatment device for cutting the living tissue (bipolar cutter) according to a second embodiment of the present invention.
Figure 45:
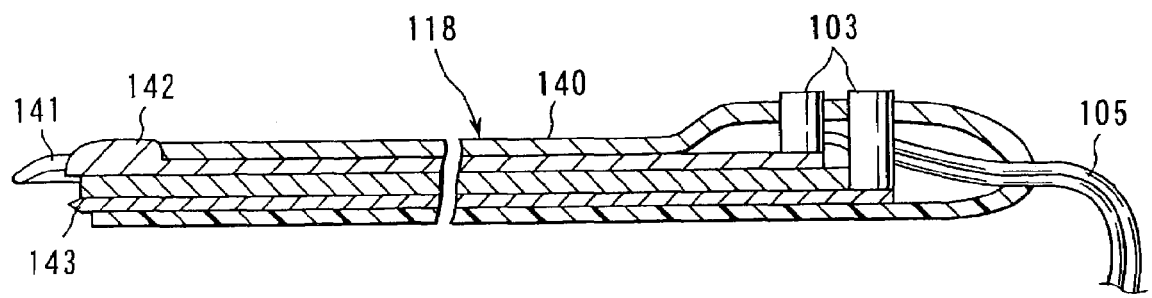
FIG. 45 is a side sectional view of the bipolar cutter of FIG. 44.

FIGS. 44 and 45 show a second embodiment of the treatment device for cutting the living tissue according to the present invention. In the above-described embodiment, the treatment device for cutting the living tissue is incorporated in the endoscopic blood vessel harvesting apparatus, but the treatment device for cutting the living tissue of the present embodiment can be inserted into the body alone and can cut the blood vessel alone.

That is, as shown in FIGS. 44 and 45, a bipolar cutter 118 as the treatment device for cutting the living tissue of the present embodiment includes:
a cutter main unit 140 to be inserted into the body;
a tip-end treatment portion 140a, disposed in the tip end of the cutter main unit 140, for cutting the blood vessel; and electrodes 142, 143, disposed in the tip-end treatment portion 140a, for electrically cutting the blood vessel. The cutter main unit 140 is formed of an insulating member (including ceramic) such as a synthetic resin material, and substantially has a flat plate shape. Moreover, the electrodes 142, 143 are electrically insulated from each other by an insulator disposed between the electrodes.

Moreover, a guide portion for guiding the blood vessel into the electrodes 142, 143 with the movement of the cutter main unit 140 in the axial direction is formed in the tip-end treatment portion 140a of the cutter main unit 140. In the present embodiment, this guide portion is formed by a notch groove (slit) 141 cut in a V shape. In this case, sides 141a, 141b forming the V shape extend upwards toward a circular arc shaped top portion in the proximal end from opposite side edges of the cutter main unit 140 in the distal end to form a tissue guide surface of the notch groove (hereinafter referred to as the V groove) 141 which tapers toward the proximal end.

Furthermore, a pair of electrodes 142, 143 disposed opposite to each other are fixed/disposed on a bottom of the V groove 141, that is, an intersection of the respective sides 141a, 141b forming the V shape. These two electrodes 142, 143 are not disposed in the same plane, and are positioned vertically opposite to each other.

Additionally, for these two electrodes, the upper electrode 142 has a surface area larger than that of the lower electrode 143. That is, the area of the upper electrode 142 in contact with the tissue is large. On the other hand, the area of the lower electrode 143 in contact with the tissue is small. As the first embodiment, the lower electrode 143 is allowed to function as an incision (cutting) electrode, and the upper electrode 142 is allowed to function as a coagulation electrode.

Moreover, a handle 102 is disposed in the proximal end of the cutter main unit 140. An electric cable 105 connected to the high-frequency generation apparatus 56 extends from the handle 102. Furthermore, switches 103 for controlling the electric supply to the electrodes 142, 143 are disposed on the handle 102.

Figure 46:
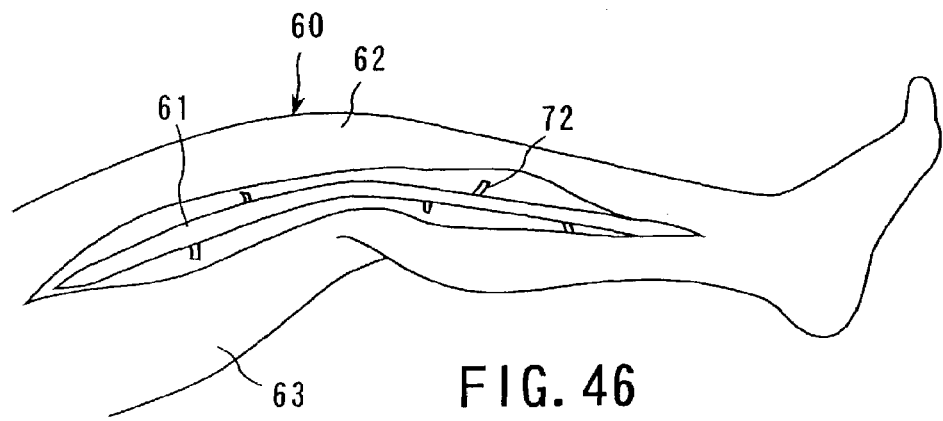
FIG. 46 is a diagram showing a state in which a leg is incised along the blood vessel
Figure 47:
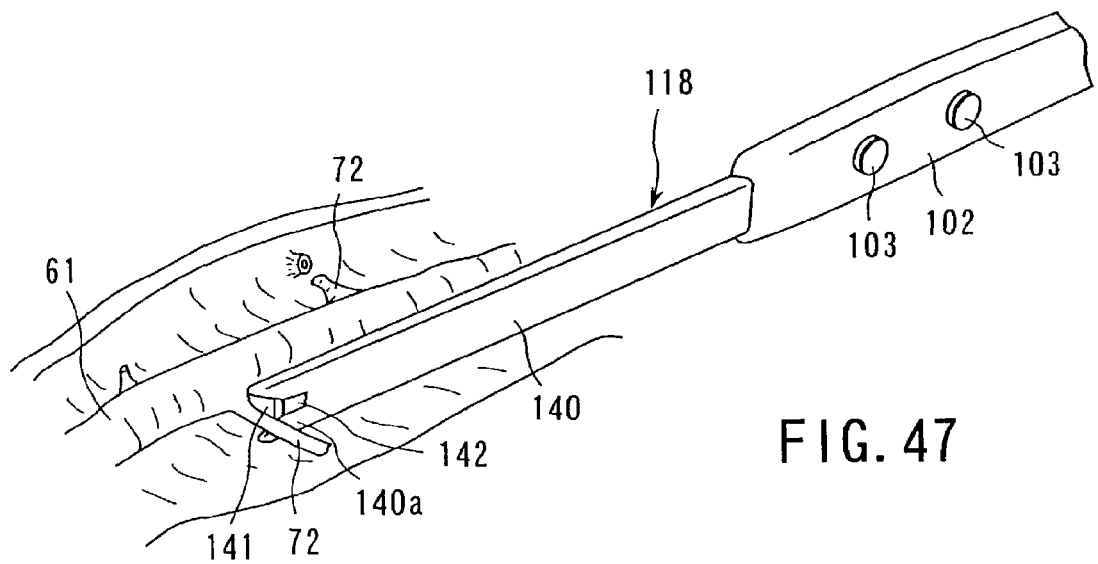
FIG. 47 is a diagram showing the use mode of the bipolar cutter of FIG. 44.
Figure 48:
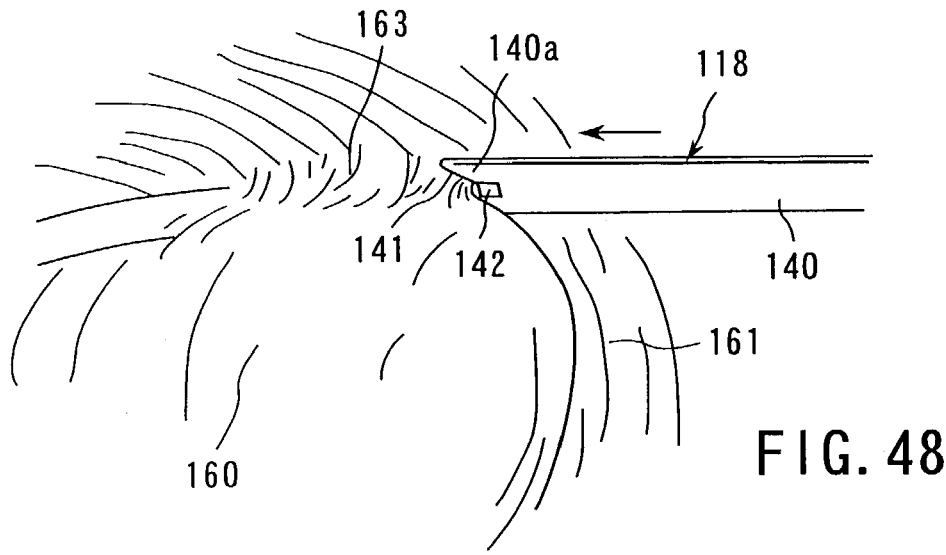
FIG. 48 is a diagram showing another use mode of the bipolar cutter of FIG. 44.

FIGS. 46 to 48 show one example of the use mode of the bipolar cutter 118. FIGS. 46 and 47 show a mode in which the bipolar cutter 118 is used to harvest the blood vessel (great saphenous vein) 61 extending to the ankle from the inguinal portion 63 of the femoral region of the leg 60. The harvesting method using the bipolar cutter 118 comprises: entirely incising the leg 60 along the blood vessel 61 to be harvested; and completely exposing the whole blood vessel 61 to be harvested. In this state, the side branch 72 is introduced into the V groove 141 as shown in FIG. 47 so as to cut the blood vessel. Also in this case, similarly to the above-described embodiment, since the V groove 141 is disposed, the bipolar cutter 118 can simply be pushed forwards to easily cut the side branch 72. Moreover, FIG. 48 shows a mode in which the bipolar cutter 118 is used in the manual operation of stripping an adhering portion 163 of an organ 160 and body wall 161. As shown, when an adhering tissue is introduced into the V groove 141 and the cutter is pushed forwards along the adhering portion 163, the adhering portion 163 of the organ 160 with the body wall 161 can easily be stripped.

As described above, also in the bipolar cutter 118 of the present embodiment, the V groove (guide portion) 141 which guides the blood vessel into the electrodes 142, 143 with the movement of the cutter main unit 140 in the axial direction is formed in the tip-end treatment portion 140a. Therefore, the cutter main unit 140 is simply moved forwards/backwards, so that the blood vessel can be approached and also cut.

FIGS. 49A to 50B show modification examples of formed configurations of the electrodes 42, 43 (142, 143) in the above-described both bipolar cutters 18, 118.

Figure 49A:
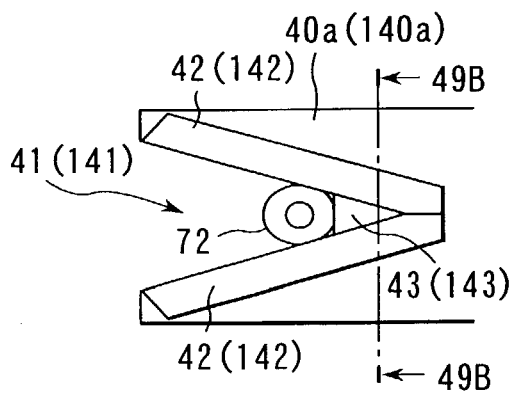
FIG. 49A is a plan view of the tip-end treatment portion showing the modification example of a formed mode of an electrode in the bipolar cutter.
Figure 49B:
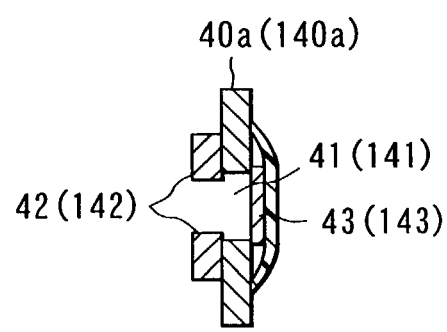
FIG. 49B is a sectional view along a line 49B-49B of FIG. 49A.

In FIGS. 49A and 49B, the body-side electrode 42 (142) is disposed over the total length of each side of the V groove 41 (141). Concretely, as shown in FIG. 49B, the body-side electrode 42 (142) is disposed in the upper edge of the wall surface of the V groove 41 (141) corresponding to each side forming the V shape. Moreover, the cut electrode 43 (143) is disposed in the intersection of the respective sides forming the V shape in the same manner as in the above-described embodiment. As clearly shown in FIG. 49B, the body-side electrode 42 (142) and cut electrode 43 (143) are not disposed in the same plane, and are positioned vertically opposite to each other.

When the body-side electrode 42 (142) is disposed over the total length of each side of the V groove 41 (141) in this manner, the surface area of the body-side electrode 42 (142) can further be set to be larger than that of the above-described embodiment. As a result, the ratio of the contact area of the body-side electrode 42 (142) to that of the cut electrode 43 (143) can be enlarged. Therefore, the incision function can further be imparted to the cut electrode 43 (143) side, and a cutting force is improved (cutting function is enhanced).

Figure 50A:
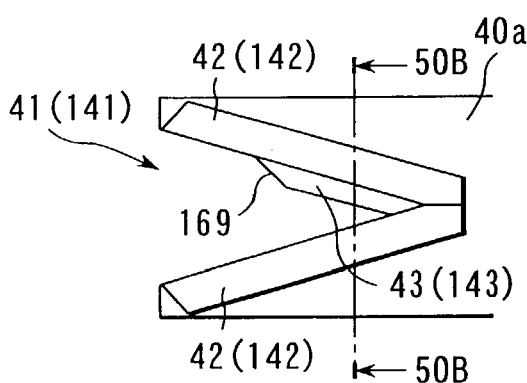
FIG. 50A is a plan view of the tip-end treatment portion showing another modification example of the formed mode of the electrode in the bipolar cutter.
Figure 50B:
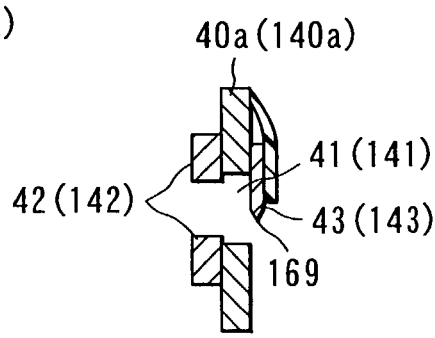
FIG. 50B is a sectional view along a line 50B-50B of FIG. 50A.

Moreover, in FIGS. 50A and 50B, the body-side electrode 42 (142) is disposed over the total length of each side of the V groove 41 (141) in the same manner as in FIGS. 49A and 49B, and the cut electrode 43 (143) is disposed opposite to the body-side electrode 42 (142) in one side of the V groove 41 (141). In this case, the cut electrode 43 (143) has a sharply tapered portion 169 in the tip end, and extends substantially over the half of the side of the V groove 41 (141).

According to this constitution, a function/effect similar to that of FIGS. 49A and 49B is obtained, and the cut electrode 43 (143) obliquely bites and cuts the tissue (blood vessel) via the tapered portion 169. Therefore, the constitution is superior in an incision force, and produces an effect, particularly when the side branch 72 is buried in the subcutaneous fat 73.

Figure 51:
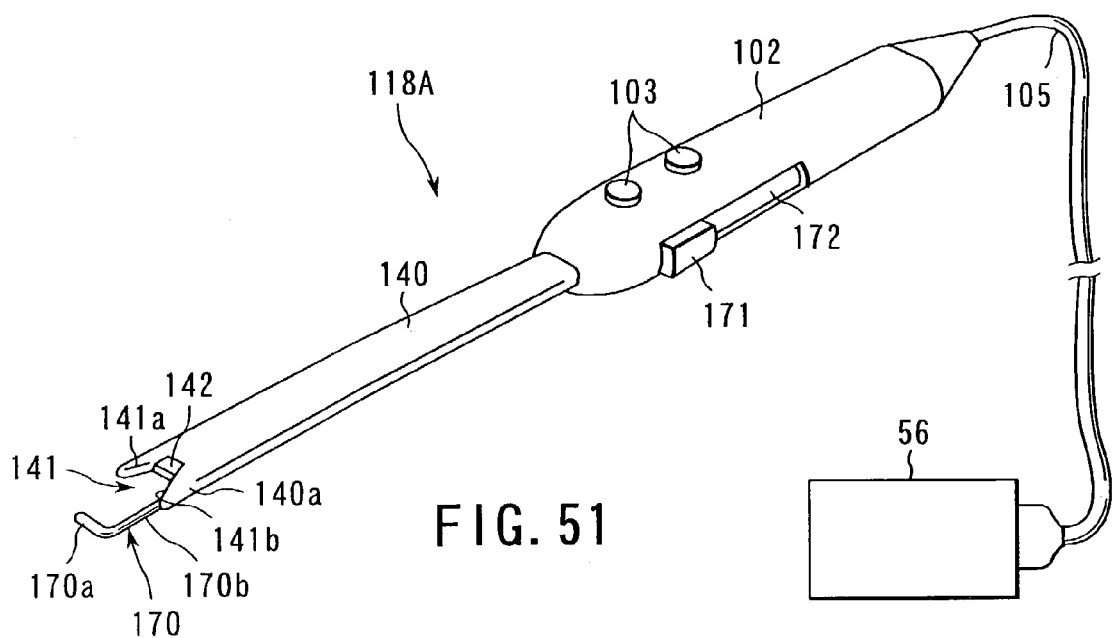
FIG. 51 is a perspective view showing the modification example of the bipolar cutter shown in FIG. 44.
Figure 52A:
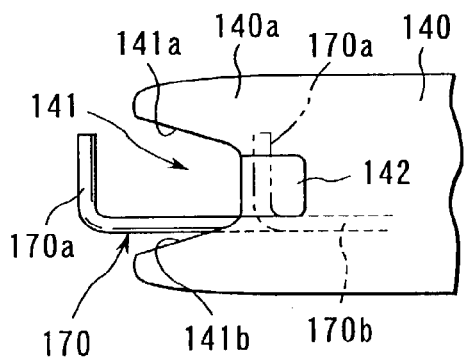
FIG. 52A is a plan view of the tip-end treatment portion of the bipolar cutter of FIG. 51.
Figure 52B:
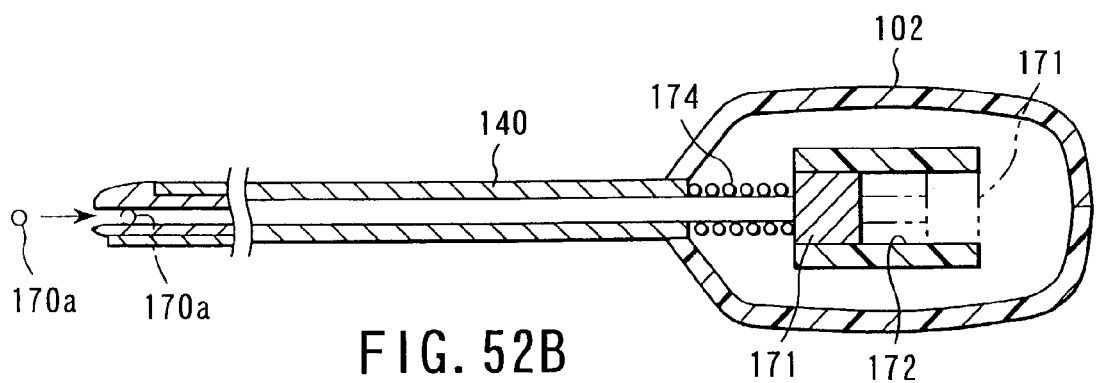
FIG. 52B is a side sectional view of the bipolar cutter of FIG. 51.

FIGS. 51 to 52B show a modification example of the bipolar cutter 118 shown in FIG. 44. As shown, a bipolar cutter 118A according to this modification example includes a blood vessel abutment portion 170 for drawing the blood vessel into the V groove 141. This blood vessel abutment portion 170 includes: a longitudinal shaft portion 170b; and a hold bar 170a which is bent substantially at right angles in the tip end of the shaft portion 170b and disposed opposite to the V groove 141. The shaft portion 170b extends over the total length of the cutter main unit 140 (passes, for example, through the cutter main unit 140), and is connected to an operation portion 171 disposed in the handle 102. The operation portion 171 can slide forwards/backwards in an elongated groove 172 formed in the handle 102. Therefore, when the operation portion 171 is slid forwards/backwards in this constitution, the shaft portion 170b is pushed/pulled, and the hold bar 170a can move with respect to the V groove 141. Moreover, urging means 174 such as a spring is disposed between the operation portion 171 and cutter main unit 140. This urging means 174 urges the operation portion 171 in a direction in which the hold bar 170a is detached from the V groove 141. It is to be noted that another constitution is the same as that of the bipolar cutter 118 shown in FIG. 40 and is denoted with the same reference numerals and description thereof is omitted.

Therefore, in this constitution, the blood vessel is positioned between the hold bar 170a and V groove 141, the operation portion 171 is slid toward the hand side against the urging force of the urging means 174 in this state, then the hold bar 170a is moved on a V groove 141 side, and the blood vessel is drawn into the V groove 141 by the hold bar 170a. Moreover, when the hold bar 170a is drawn into a position shown, for example, by a broken line in FIG. 52A, the blood vessel can be pressed into contact with the electrodes 142, 143.

As described above, according to the present modification example, the blood vessel is further easily cut by a synergistic effect of guide functions by the V groove 141 and hold bar 170a. In addition, high-efficiency hemostasis can be achieved since the blood vessel is cut while being compressed.

Figure 53:
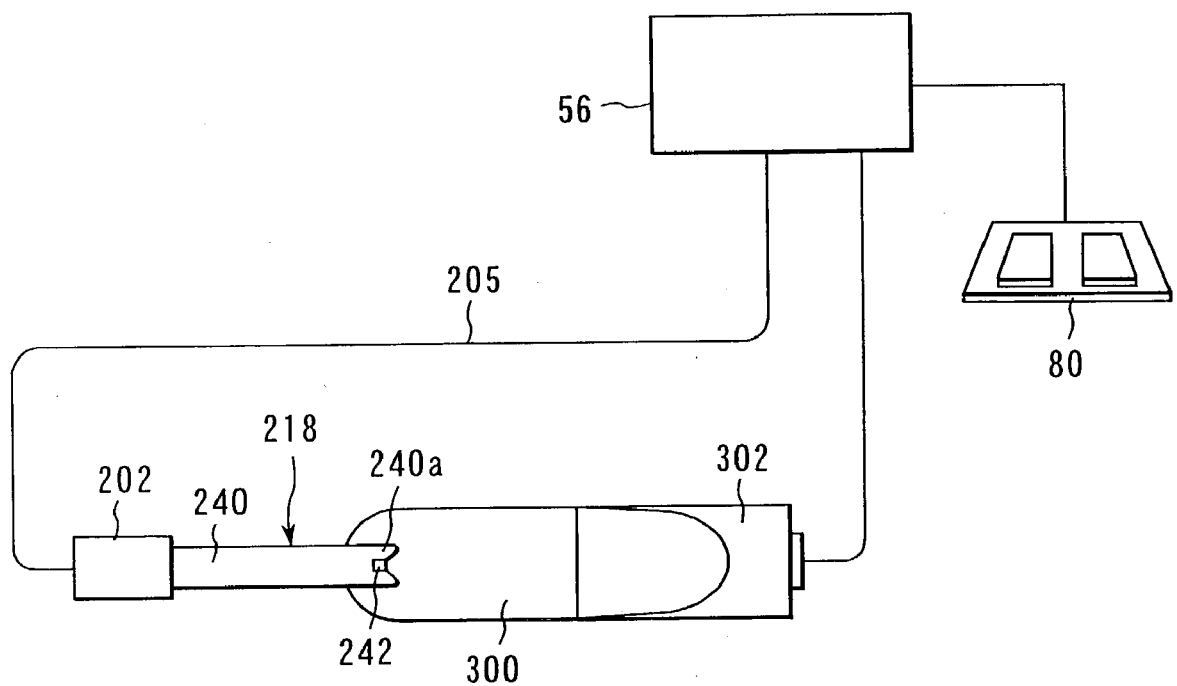
FIG. 53 is a schematic constitution diagram of the treatment device for cutting the living tissue (monopolar cutter) according to a third embodiment of the present invention.
Figure 54A:
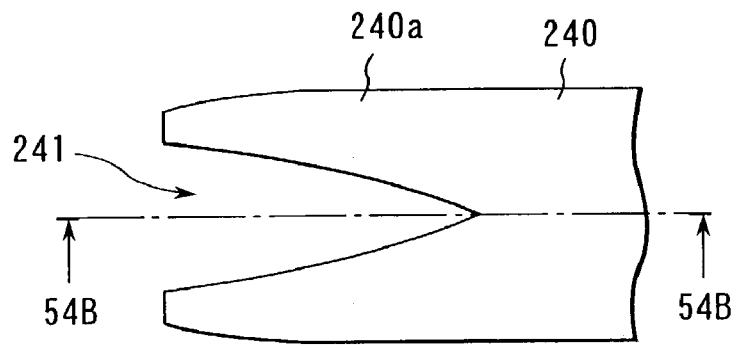
FIG. 54A is a plan view of the tip-end treatment portion of the treatment device for cutting the living tissue of FIG. 53.
Figure 54B:
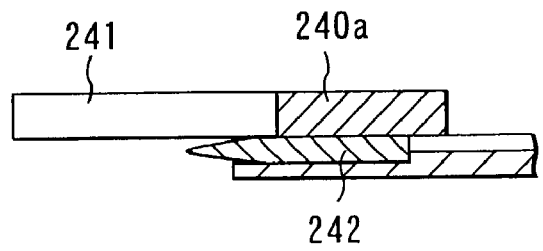
FIG. 54B is a sectional view along line 54B-54B of FIG. 54A.

FIGS. 53 to 54B show a third embodiment of the treatment device for cutting the living tissue according to the present invention. The treatment device for cutting the living tissue in the above-described embodiment is of a bipolar type, but a treatment device for cutting the living tissue 218 of the present embodiment is of a monopolar type.

That is, as shown in FIG. 53, the treatment device for cutting the living tissue 218 includes: a cutter main unit 240 which is to be inserted into the body; a tip-end treatment portion 240a which is disposed in the tip end of the cutter main unit 240 so as to cut the blood vessel; and an electrode (monopolar) 242 which is disposed in the tip-end treatment portion 240a and which electrically cuts the blood vessel together with a counter electrode plate 302 disposed in the tip-end treatment portion 240a in contact with a living tissue 300. The cutter main unit 240 is formed of the insulating member (e.g., ceramic) of the synthetic resin material and substantially forms a flat plate shape.

Moreover, as clearly shown in FIGS. 54A and 54B, the guide portion for guiding the blood vessel into the electrode 242 with the movement of the cutter main unit 240 in the axial direction is formed in the tip-end treatment portion 240a of the cutter main unit 240. In the present embodiment, this guide portion is formed by a notch groove (slit) 241 cut in the V shape. Furthermore, the electrode 242 is fixed/disposed in the bottom of the V groove 241, that is, the intersection of the respective sides which form the V shape.

Furthermore, a handle 202 is disposed in the proximal end of the cutter main unit 240. An electric cable 205 connected to the high-frequency generation apparatus 56 extends from this handle 202. Additionally, a foot switch 80 for controlling the electricity supply to the electrode 242 is connected to the high-frequency generation apparatus 56.

Even with the monopolar constitution, when the V groove 241 is formed in the tip-end treatment portion 240a, the function/effect similar to that of the above-described bipolar constitution can be obtained.

It is to be noted that needless to say the present invention is not limited to the above-described embodiments and can variously be modified/implemented without departing from the scope. For example, although the present invention is applied to the blood vessel harvesting apparatus in the above-described embodiments, the present invention can also be applied to the harvesting of living tissues other than the blood vessel.

What is claimed is:

1. A treatment device for cutting living tissue, comprising:
an insertion member having distal and proximal ends, at least the distal end being inserted into a body cavity, the insertion member including a notch groove formed in the distal end, the notch groove having
an opening formed in an outer surface of the distal end,
a bottom portion, and
first and second guide portions which are extended to the bottom portion from the opening, the first guide portion being extended from the opening for receiving the living tissue from the opening, and second guide portion being extended from the first guide portion to the bottom portion and having a narrower width than that of the first guide portion for guiding the living tissue from the first guide portion to the bottom portion, the notch groove having a non-variable inner space defined by the opening, the bottom portion, and the first and second guide portions, and
at least two electrodes separately provided on opposite faces of the bottom portion and aligned with the second guide portion of the distal end of the insertion member, the device being so structured that, when the living tissue is inserted into the notch groove and guided to the bottom portion from the opening along the guide portion, as the distal end of the insertion member is advanced into the body cavity, the living tissue is electrically cut by a first electrode having a first contact area for contact with the living tissue that is smaller than a second contact area of a second electrode of the at least two electrodes, wherein the bottom portion further comprises a forward surface extending along a first plane, the first plane being substantially perpendicular to an axial direction of the insertion member, wherein the first contact area comprises a first portion positioned on the forward surface and the second contact area comprises a second portion positioned on the forward surface, and wherein the second portion of the second contact area extends toward the first portion of the first contact area along the forward surface.

2. The treatment device according to claim 1, wherein the opening, first and second guide portions and a bottom portion of the notch groove are integrally formed of a one-piece member.

3. The treatment device according to claim 1, wherein the opening of the notch groove has a maximum opening width which is smaller than a maximum length in a direction normal to a longitudinal axial direction of the insertion member.

4. The treatment device according to claim 1, wherein the first guide portion has an inclined flat surface.

5. The treatment device according to claim 1, wherein said at least two electrodes are provided on the bottom portion of the notch groove.

6. The treatment device according to claim 5, wherein the at least two electrodes provided on the bottom portion extend onto the second guide portion of the notch groove.

7. The treatment device according to claim 1, wherein the notch groove has a shape symmetrical with respect to a longitudinal central axis of the insertion member.

8. The treatment device for cutting the living tissue according to claim 1, wherein the second guide portion guides the living tissue onto the first and second electrodes with movement of the insertion member in an axial direction of the insertion member or a direction crossing at right angles to the axial direction.

9. The treatment device for cutting the living tissue according to claim 1, wherein the first guide portion has a V shape, and guides the living tissue, and the second guide portion extends in a parallel with an axial direction of the insertion member.

10. The treatment device for cutting the living tissue according to claim 9, wherein the first and second electrodes are disposed in the bottom portion.

11. The treatment device for cutting the living tissue according to claim 1, wherein the two electrodes are not disposed in the same plane.

12. The treatment device for cutting the living tissue according to claim 1, wherein portions other than the electrodes are formed of transparent materials.

13. A blood vessel harvesting apparatus comprising:
a sheath which can be inserted into a cavity through a cut skin portion; and
a blood vessel harvesting portion which moves forwards/backwards in the sheath to harvest a blood vessel in the cavity, wherein the blood vessel harvesting portion comprises: a bipolar cutting device which incises a living tissue; and a holder axially extendable independently and relative to the bipolar cutting device to hold and harvest the blood vessel, the bipolar cutting device comprises:
a cutter main unit insertable into a body through and along an inner peripheral surface of the sheath and being arc-shaped;
a tip-end treatment portion disposed at a tip end of the cutter main unit to cut the living tissue, the tip-end treatment portion having a forward surface; and
a pair of electrodes disposed at the tip-end treatment portion, on opposite concave and convex faces of the cutter main unit, the electrodes having different shapes from each other in a contact area in contact with the living tissue, and a distance between the electrode having a large contact area and the holder is longer than that between the electrode having a small contact area and the holder, wherein each of the pair of electrodes comprises a front portion located on a first plane, the first plane being substantially perpendicular to a moving direction of the bipolar cutting device and being positioned on the forward surface of the tip-end treatment portion, and wherein the front portion of the electrode having the large contact area extends along the first plane toward the front portion of the electrode having the small contact area.

14. A blood vessel harvesting apparatus comprising:
a sheath which can be inserted into a cavity through a cut skin portion; and
a blood vessel harvesting portion which moves forwards/backwards in the sheath to harvest a blood vessel in the cavity, wherein the blood vessel harvesting portion comprises a bipolar cuffing device which cuts a living tissue, and a holder which holds a harvesting object blood vessel; an insertion member having distal and proximal ends, at least the distal end being inserted into a body cavity; the insertion member including;
a notch groove formed in the distal end, the notch groove having an opening formed in an outer surface of the distal end,
a bottom portion and a guide portion which is extended to the bottom portion from the opening, the notch groove having a non-vanable inner space defined by the opening, the bottom portion, and the guide portion; and
at least two electrodes provided on opposite faces of the bottom portion and aligned with the guide portion of the distal end of the insertion member, wherein the living tissue is inserted into the notch groove and guided to the bottom portion from the opening along the guide portion, as the distal end of the insertion member is advanced in the body cavity, and electrically cut by a first electrode having a first contact area for contact with the living tissue that is smaller than a second contact area of a second electrode of the at least two electrodes, wherein the bottom portion further comprises a forward surface extending along a first plane, the first plane being substantially perpendicular to a moving direction of the bipolar cutting device, wherein the first contact area comprises a first portion positioned on the forward surface and the second contact area comprises a second portion positioned on the forward surface, and wherein the second portion of the second contact area extends toward the first portion of the first contact area along the forward surface.

15. An apparatus for performing an operation on living tissue, comprising:
a trocar having a guide tube;
a treatment sheath configured to be received within the guide tube of the trocar, the sheath including at least one treatment device channel; and
a respective treatment device configured to be received within the treatment device channel, a first respective treatment device being a treatment device for cutting the living tissue, the first treatment device including:
an insertion member having distal and proximal ends, at least the distal end being inserted into a body cavity;
the insertion member including a notch groove formed in the distal end, the notch groove having an opening formed in an outer surface of the distal end, a bottom portion and a guide portion which is extended to the bottom portion from the opening, the notch groove having a non-variable inner space defined by the opening, the bottom portion, and the guide portion; and at least two electrodes provided on opposite faces of the bottom portion and aligned with the guide portion of the distal end of the insertion member, wherein the living tissue is inserted into the notch groove and guided to the bottom portion from the opening along the guide portion, as the distal end of the insertion member is advanced in the body cavity, and electrically cut by a first electrode having a first contact area for contact with the living tissue that is smaller than a second contact area of a second electrode of the at least two electrodes, wherein the bottom portion further comprises a forward surface extending along a first plane, the first plane being substantially perpendicular to an axial direction of the insertion member, wherein the first contact area comprises a first portion positioned on the forward surface and the second contact area comprises a second portion positioned on the forward surface, and wherein the second portion of the second contact area extends toward the first portion of the first contact area along the forward surface.

16. The apparatus according to claim 15, wherein the guide portion has a V shape, and guides the living tissue into the electrode by a wall surface of the notch groove corresponding to each side which forms the V shape.

17. The apparatus according to claim 15, wherein the treatment sheath further includes an endoscope channel structured to receive an endoscope for viewing the living tissue.

18. The apparatus according to claim 15, wherein the at least one treatment device channel includes a plurality of treatment device channels structured to receive aplurality of treatment devices.

19. The apparatus according to claim 18, wherein the treatment sheath further includes an endoscope channel structured to receive an endoscope for viewing the living tissue, and the treatment devices include an endoscope wiper operable to clean a distal end of the endoscope.

20. The apparatus according to claim 18, wherein the treatment devices include a tissue holder for holding the living tissue during a cutting operation.

* * * * *